(12) United States Patent
Jackson et al.

(10) Patent No.: US 6,756,493 B1
(45) Date of Patent: Jun. 29, 2004

(54) NUCLEIC ACID SEQUENCE AND USES THEREOF

(75) Inventors: W. James Jackson, Marriotsville, MD (US); Andrea M. Harris, Frederick, MD (US)

(73) Assignee: Antex Biologics, Inc., Gaithersburg, MD (US)

( * ) Notice: Subject to any disclaimer, the term of this patent is extended or adjusted under 35 U.S.C. 154(b) by 0 days.

(21) Appl. No.: 09/388,090

(22) Filed: Aug. 31, 1999

Related U.S. Application Data

(60) Provisional application No. 60/098,685, filed on Sep. 1, 1998.

(51) Int. Cl.[7] .................. C07H 21/04; C07H 21/02; C12N 15/00; C12P 29/06; A61K 39/02
(52) U.S. Cl. ............. 536/23.7; 536/23.1; 536/24.32; 424/234.1; 424/184.1; 424/249.1; 435/320.1; 435/69.1; 435/71.1
(58) Field of Search ............. 536/23.7, 23.1, 536/24.32; 435/320.1, 69.1; 424/184.1, 269.1, 234.1; 530/350, 825, 826

(56) References Cited

U.S. PATENT DOCUMENTS

| | | | |
|---|---|---|---|
| 4,681,761 A | | 7/1987 | Mietzner et al. |
| 4,900,659 A | | 2/1990 | Lo et al. .................. 435/6 |
| 5,378,606 A | * | 1/1995 | Stern et al. ................ 435/6 |
| 6,096,529 A | * | 8/2000 | Gilbert et al. ........... 435/252.3 |
| 6,287,568 B1 | * | 9/2001 | Wang et al. ............ 424/197.11 |
| 2002/0149763 A1 | * | 10/2002 | Tsukada ...................... 356/73 |

FOREIGN PATENT DOCUMENTS

| | | | |
|---|---|---|---|
| WO | WO 90/06696 | * | 6/1990 |
| WO | WO 90/06696 A2 | | 6/1990 |
| WO | WO 9213871 | * | 8/1992 |
| WO | WO 9514772 | * | 6/1995 |
| WO | WO 95/31549 | * | 11/1995 |
| WO | WO 9818945 | * | 5/1998 |
| WO | WO 98/42721 A1 | | 10/1998 |
| WO | WO99/55872 A1 | | 11/1999 |
| WO | WO 99/57280 | | 11/1999 |

OTHER PUBLICATIONS

Harlow et al. In: Antibodies: A Laboratory Manual. Cold Spring Harbor Laboratory. p. 76, 1988.*
Strategene Product Catalog, 1991 (two pages).*
Halter et al. EMBO J. *: 2737–2744, 1989.*
Pohlner et al. Nature 325: 458–462, 1987.*
Plaut et al. Science 190: 1103–1105, 1975.*
Bachovchin et al. J. Biol. Chem. 265: 3738–3743, 1990.*
Cleton–Jensen et al. Mol. Gen. Genet. 229 (2): 206–212— search report, 1991.*
Lehninger AL. Principles of Biochemistry, Worth Publishers, Inc., New York, Chapter 27, pp. 793–836, 1982.*
Karkhanis et al. Infect. Immun. 25: 635–644, abstract, 1979.*
Zhang et al. Genetics 143: 941–952, Jun. 1996.*
Poulsen et al. J. Bacteriol. 174: 2913–2921, 1992.*
Koomey et al., 1984, Infec. Immunol. 43: 101–107.
Marshall et al., 1999, Diag. Microbiol. Infect. Dis., 33:181–186.
Barrett et al., 1998, Antimicrobial Agents and Chemotherapy, 42(7):1529–1536.
Jones et al., 1998, DDT, 3(11):495–504.
Fabret et al., 1998, J. Bacteriol, 180(23):6375–6383.

* cited by examiner

*Primary Examiner*—S. Devi
(74) *Attorney, Agent, or Firm*—Jones Day

(57) ABSTRACT

The invention discloses the Neisseria spp. NGSP polypeptide, polypeptides derived therefrom (NGSP-derived polypeptides), nucleotide sequences encoding said polypeptides, and antibodies that specifically bind the NGSP polypeptide and/or NGSP-derived polypeptides. Also disclosed are prophylactic or therapeutic compositions, including antigenic, preferably immunogenic compositions, e.g., vaccines, comprising NGSP polypeptide and/or a NGSP-derived polypeptide or antibodies thereto. The invention additionally discloses methods of inducing an immune response to Neisseria and Neisseria NGSP polypeptide and an NGSP-derived polypeptide in animals.

5 Claims, 2 Drawing Sheets

SEQUENCE LISTING

<160> NUMBER OF SEQ ID NOS: 10

<210> SEQ ID NO 1
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 1
aggcagaggg aattcatgtt caaaaaatac caatacttcg ctttgg         46

<210> SEQ ID NO 2
<211> LENGTH: 69
<212> TYPE: DNA
<213> ORGANISM: Artificial Sequence
<220> FEATURE:
<223> OTHER INFORMATION: Description of Artificial Sequence: Primer

<400> SEQUENCE: 2
aggcagaggg tcgacttaat ggtgatggtg atggtgttga cggggacttg ccctgacggc    60
taggatttc                                                           69

<210> SEQ ID NO 3
<211> LENGTH: 1395
<212> TYPE: DNA
<213> ORGANISM: Neisseria gonorrhoeae

<400> SEQUENCE: 3
gtgttcaaaa aataccaata cttcgctttg gcggcactgt gtgccgcctt gctggcaggc     60
tgcgaaaagg caggcagctt tttcggtgcg acaaaaaag aagcatcctt cgtagaacgc    120
atcgaacaca ccaaagacga cggcagtgtc agtatgctgc tgcccgactt tgcccaactg    180
gttcaaagcg aaggcccggc agtcgtcaat attcaggcag ccccgccc gcgcacccaa    240 aacggcagcg gcaatgccga aaccgattcc gacccgcttg ccgacagcga cccgttctac    300 gaattttca acgcctcgt cccgaacatg cccgaaatcc cccaagaaga agcagatgac    360
ggcggattga acttcggttc gggcttcatc atcagcaaaa acggctacat cctgaccaat    420
acccacgtcg ttgccggtat gggcagtatc aaagtcctgc tcaacgacaa agcgaatat    480 accgccaaac tcatcggttc ggatgtccaa tccgatgtcg cccttctgaa atcgacgca    540 acggaagagc tacccgtcgt caaaatcggc aatcccaaaa atttgaaacc gggcgaatgg    600
gtcgctgcca tcggcgcgcc cttcggcttt gacaacagcg tgaccgccgg catcgtgtcc    660
gccaaagcca aagcctgcc caacgaaagc tacacaccct tcatccaaac cgacgttgcc    720
atcaatccgg gcaattccgg cggcccgctg ttcaacttaa aggacaggt cgtcggcatc    780 aattcgcaaa tatacagccg cagcggcgga ttcatgggca tctccttgc catcccgatt    840 gacgttgcca tgaatgtcgc cgaacagctg aaaaacaccg gcaaagtcca acgcggacaa    900
ctgggcgtga ttattcagga agtatcctac ggtttggcac agtcgttcgg tctggataaa    960
gccagcggcg cattgattgc caaaatcctt cccggcagcc ccgcagaacg tgccggcctg   1020
caggcgggcg acatcgtcct cagcctgac ggcgagaaa tacgttcttc cggcgacctt   1080
cccgtcatgg tcggcgccat tacgccggga aaagaagtca gcctcggcgt atggcgcaaa   1140
ggcgaagaaa tcacaatcaa agccaagctg ggcaacgccg ccgagcatac cggcgcatca   1200
tccaaaacag atgaagcccc ctacaccgaa cagcaatccg gtacgttctc ggtcgaatcc   1260

-continued

```
gcaggcatta ccctttcagac acataccgac agcagcggca aacacctcgt cgtcgtacgg    1320
gtttccgacg cggcagaacg cgcaggctta aggcacggcg acgaaatcct agccgtcagg    1380
gcaagtcccc gtcaa                                                     1395
```

<210> SEQ ID NO 4
<211> LENGTH: 465
<212> TYPE: PRT
<213> ORGANISM: Neisseria gonorrhoeae

<400> SEQUENCE: 4

| Val | Phe | Lys | Lys | Tyr | Gln | Tyr | Phe | Ala | Leu | Ala | Ala | Leu | Cys | Ala | Ala |
|---|---|---|---|---|---|---|---|---|---|---|---|---|---|---|---|
| 1 | | | | 5 | | | | | 10 | | | | | 15 | |

Leu Leu Ala Gly Cys Glu Lys Ala Gly Ser Phe Phe Gly Ala Asp Lys
            20                  25                  30

Lys Glu Ala Ser Phe Val Glu Arg Ile Glu His Thr Lys Asp Asp Gly
        35                  40                  45

Ser Val Ser Met Leu Leu Pro Asp Phe Ala Gln Leu Val Gln Ser Glu
    50                  55                  60

Gly Pro Ala Val Val Asn Ile Gln Ala Ala Pro Ala Pro Arg Thr Gln
65                  70                  75                  80

Asn Gly Ser Gly Asn Ala Glu Thr Asp Ser Asp Pro Leu Ala Asp Ser
                85                  90                  95

Asp Pro Phe Tyr Glu Phe Phe Lys Arg Leu Val Pro Asn Met Pro Glu
            100                 105                 110

Ile Pro Gln Glu Glu Ala Asp Asp Gly Gly Leu Asn Phe Gly Ser Gly
        115                 120                 125

Phe Ile Ile Ser Lys Asn Gly Tyr Ile Leu Thr Asn Thr His Val Val
    130                 135                 140

Ala Gly Met Gly Ser Ile Lys Val Leu Leu Asn Asp Lys Arg Glu Tyr
145                 150                 155                 160

Thr Ala Lys Leu Ile Gly Ser Asp Val Gln Ser Asp Val Ala Leu Leu
                165                 170                 175

Lys Ile Asp Ala Thr Glu Glu Leu Pro Val Val Lys Ile Gly Asn Pro
            180                 185                 190

Lys Asn Leu Lys Pro Gly Glu Trp Val Ala Ile Gly Ala Pro Phe
        195                 200                 205

Gly Phe Asp Asn Ser Val Thr Ala Gly Ile Val Ser Ala Lys Gly Arg
    210                 215                 220

Ser Leu Pro Asn Glu Ser Tyr Thr Pro Phe Ile Gln Thr Asp Val Ala
225                 230                 235                 240

Ile Asn Pro Gly Asn Ser Gly Pro Leu Phe Asn Leu Lys Gly Gln
                245                 250                 255

Val Val Gly Ile Asn Ser Gln Ile Tyr Ser Arg Ser Gly Gly Phe Met
            260                 265                 270

Gly Ile Ser Phe Ala Ile Pro Ile Asp Val Ala Met Asn Val Ala Glu
        275                 280                 285

Gln Leu Lys Asn Thr Gly Lys Val Gln Arg Gly Gln Leu Gly Val Ile
    290                 295                 300

Ile Gln Glu Val Ser Tyr Gly Leu Ala Gln Ser Phe Gly Leu Asp Lys
305                 310                 315                 320

Ala Ser Gly Ala Leu Ile Ala Lys Ile Leu Pro Gly Ser Pro Ala Glu
                325                 330                 335

Arg Ala Gly Leu Gln Ala Gly Asp Ile Val Leu Ser Leu Asp Gly Gly

-continued

```
                    340                 345                 350
Glu Ile Arg Ser Ser Gly Asp Leu Pro Val Met Val Gly Ala Ile Thr
                355                 360                 365
Pro Gly Lys Glu Val Ser Leu Gly Val Trp Arg Lys Gly Glu Ile
    370                 375                 380
Thr Ile Lys Ala Lys Leu Gly Asn Ala Ala Glu His Thr Gly Ala Ser
385                 390                 395                 400
Ser Lys Thr Asp Glu Ala Pro Tyr Thr Glu Gln Ser Gly Thr Phe
                405                 410                 415
Ser Val Glu Ser Ala Gly Ile Thr Leu Gln Thr His Thr Asp Ser Ser
                420                 425                 430
Gly Lys His Leu Val Val Val Arg Val Ser Asp Ala Ala Glu Arg Ala
                435                 440                 445
Gly Leu Arg His Gly Asp Glu Ile Leu Ala Val Arg Ala Ser Pro Arg
                450                 455                 460
Gln
465

<210> SEQ ID NO 5
<211> LENGTH: 1242
<212> TYPE: DNA
<213> ORGANISM: Neisseria gonorrhoeae

<400> SEQUENCE: 5
atgctgctgc cgactttgc ccaactggtt caaagcgaag gcccggcagt cgtcaatatt      60
caggcagccc ccgccccgcg cacccaaaac ggcagcggca tgccgaaac cgattccgac     120
ccgcttgccg acagcgaccc gttctacgaa tttttcaaac gcctcgtccc gaacatgccc     180
gaaatccccc aagaagaagc agatgacggc ggattgaact tcggttcggg cttcatcatc     240
agcaaaaacg ctacatcct gaccaatacc cacgtcgttg ccggtatggg cagtatcaaa     300
gtcctgctca cgacaagcg cgaatatacc gccaaactca tcggttcgga tgtccaatcc     360
gatgtcgccc ttctgaaaat cgacgcaacg gaagagctac ccgtcgtcaa atcggcaat     420
cccaaaaatt tgaaaccggg cgaatgggtc gctgccatcg gcgcgcccct tcggctttgac    480
aacagcgtga ccgccggcat cgtgtccgcc aaaggcagaa gcctgcccaa cgaaagctac     540
acaccttca tccaaaccga cgttgccatc aatccgggca attccggcgg cccgctgttc     600
aacttaaaag acaggtcgt cggcatcaat tcgcaaatat acagccgcag cggcggattc     660
atgggcatct cctttgccat cccgattgac gttgccatga atgtcgccga acagctgaaa     720
aacaccggca agtccaacg cggacaactg ggcgtgatta ttcaggaagt atcctacggt     780
ttggcacagt cgttcggtct ggataaagcc agcggcgcat tgattgccaa atccttccc     840
ggcagccccg cagaacgtgc cggcctgcag gcgggcgaca tcgtcctcag cctcgacggc     900
ggagaaatac gttcttccgg cgaccttccc gtcatggtcg cgccattac gccgggaaaa     960
gaagtcagcc tcggcgtatg gcgcaaaggc gaagaaatca caatcaaagc caagctgggc    1020
aacgccgccg agcataccgg cgcatcatcc aaaacagatg aagcccccta caccgaacag    1080
caatccggta cgttctcggt cgaatccgca ggcattaccc ttcagacaca taccgacagc    1140
agcggcaaac acctcgtcgt cgtacgggtt ccgacgcgg cagaacgcgc aggcttaagg    1200
cacggcgacg aaatcctagc cgtcagggca agtccccgtc aa                     1242

<210> SEQ ID NO 6
<211> LENGTH: 414
```

-continued

<212> TYPE: PRT
<213> ORGANISM: Neisseria gonorrhoeae

<400> SEQUENCE: 6

```
Met Leu Leu Pro Asp Phe Ala Gln Leu Val Gln Ser Glu Gly Pro Ala
  1               5                  10                  15

Val Val Asn Ile Gln Ala Ala Pro Ala Pro Arg Thr Gln Asn Gly Ser
             20                  25                  30

Gly Asn Ala Glu Thr Asp Ser Asp Pro Leu Ala Asp Ser Asp Pro Phe
         35                  40                  45

Tyr Glu Phe Phe Lys Arg Leu Val Pro Asn Met Pro Glu Ile Pro Gln
 50                  55                  60

Glu Glu Ala Asp Asp Gly Gly Leu Asn Phe Gly Ser Gly Phe Ile Ile
 65                  70                  75                  80

Ser Lys Asn Gly Tyr Ile Leu Thr Asn Thr His Val Val Ala Gly Met
             85                  90                  95

Gly Ser Ile Lys Val Leu Leu Asn Asp Lys Arg Glu Tyr Thr Ala Lys
        100                 105                 110

Leu Ile Gly Ser Asp Val Gln Ser Asp Val Ala Leu Leu Lys Ile Asp
        115                 120                 125

Ala Thr Glu Glu Leu Pro Val Val Lys Ile Gly Asn Pro Lys Asn Leu
130                 135                 140

Lys Pro Gly Glu Trp Val Ala Ile Gly Ala Pro Phe Gly Phe Asp
145                 150                 155                 160

Asn Ser Val Thr Ala Gly Ile Val Ser Ala Lys Gly Arg Ser Leu Pro
                165                 170                 175

Asn Glu Ser Tyr Thr Pro Phe Ile Gln Thr Asp Val Ala Ile Asn Pro
            180                 185                 190

Gly Asn Ser Gly Gly Pro Leu Phe Asn Leu Lys Gly Gln Val Val Gly
        195                 200                 205

Ile Asn Ser Gln Ile Tyr Ser Arg Ser Gly Gly Phe Met Gly Ile Ser
210                 215                 220

Phe Ala Ile Pro Ile Asp Val Ala Met Asn Val Ala Glu Gln Leu Lys
225                 230                 235                 240

Asn Thr Gly Lys Val Gln Arg Gly Gln Leu Gly Val Ile Ile Gln Glu
                245                 250                 255

Val Ser Tyr Gly Leu Ala Gln Ser Phe Gly Leu Asp Lys Ala Ser Gly
            260                 265                 270

Ala Leu Ile Ala Lys Ile Leu Pro Gly Ser Pro Ala Glu Arg Ala Gly
        275                 280                 285

Leu Gln Ala Gly Asp Ile Val Leu Ser Leu Asp Gly Gly Glu Ile Arg
290                 295                 300

Ser Ser Gly Asp Leu Pro Val Met Val Gly Ala Ile Thr Pro Gly Lys
305                 310                 315                 320

Glu Val Ser Leu Gly Val Trp Arg Lys Gly Glu Ile Thr Ile Lys
                325                 330                 335

Ala Lys Leu Gly Asn Ala Ala Glu His Thr Gly Ala Ser Ser Lys Thr
            340                 345                 350

Asp Glu Ala Pro Tyr Thr Glu Gln Gln Ser Gly Thr Phe Ser Val Glu
        355                 360                 365

Ser Ala Gly Ile Thr Leu Gln Thr His Thr Asp Ser Ser Gly Lys His
        370                 375                 380

Leu Val Val Val Arg Val Ser Asp Ala Ala Glu Arg Ala Gly Leu Arg
385                 390                 395                 400
```

-continued

```
His Gly Asp Glu Ile Leu Ala Val Arg Ala Ser Pro Arg Gln
            405                 410

<210> SEQ ID NO 7
<211> LENGTH: 51
<212> TYPE: PRT
<213> ORGANISM: Neisseria gonorrhoeae

<400> SEQUENCE: 7

Val Phe Lys Lys Tyr Gln Tyr Phe Ala Leu Ala Ala Leu Cys Ala Ala
  1               5                  10                  15

Leu Leu Ala Gly Cys Glu Lys Ala Gly Ser Phe Phe Gly Ala Asp Lys
             20                  25                  30

Lys Glu Ala Ser Phe Val Glu Arg Ile Glu His Thr Lys Asp Asp Gly
         35                  40                  45

Ser Val Ser
     50

<210> SEQ ID NO 8
<211> LENGTH: 153
<212> TYPE: DNA
<213> ORGANISM: Neisseria gonorrhoeae

<400> SEQUENCE: 8
gtgttcaaaa ataccaata cttcgctttg gcggcactgt gtgccgcctt gctggcaggc        60
tgcgaaaagg caggcagctt tttcggtgcg gacaaaaaag aagcatcctt cgtagaacgc      120
atcgaacaca ccaaagacga cggcagtgtc agt                                   153

<210> SEQ ID NO 9
<211> LENGTH: 10
<212> TYPE: PRT
<213> ORGANISM: Neisseria gonorrhoeae

<400> SEQUENCE: 9

Val Phe Lys Lys Tyr Gln Tyr Phe Ala Leu
  1               5                  10

<210> SEQ ID NO 10
<211> LENGTH: 11
<212> TYPE: PRT
<213> ORGANISM: Neisseria gonorrhoeae

<400> SEQUENCE: 10

Glu Ile Leu Ala Val Arg Ala Ser Pro Arg Gln
  1               5                  10
```

US 6,756,493 B1

NUCLEIC ACID SEQUENCE AND USES THEREOF

Figure 1:
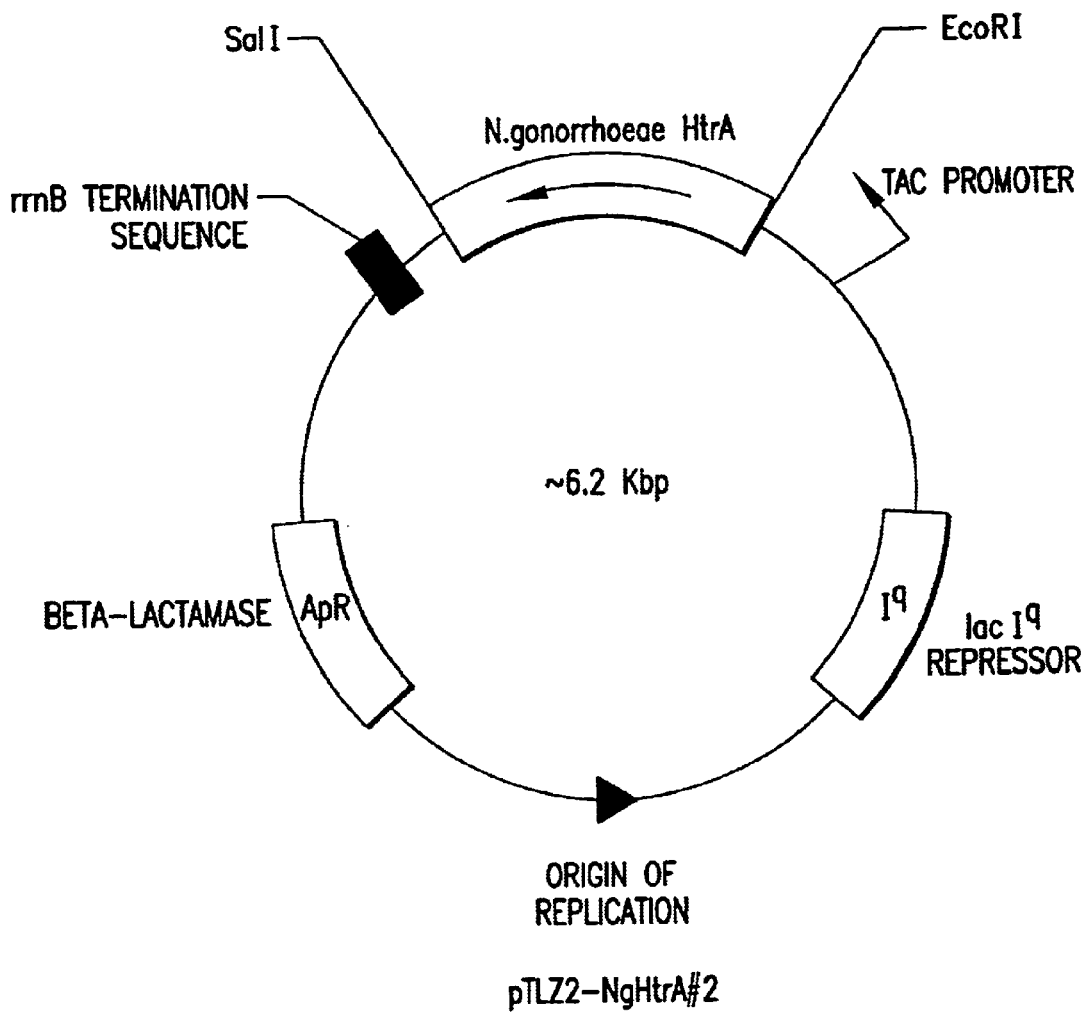

This application claims priority benefits of provisional U.S. application Ser. No. 60/098,685, filed Sep. 1, 1998, the entire disclosure of which is incorporated by reference herein.

1. INTRODUCTION

The present invention relates generally to a polypeptide of Neisseria spp., e.g., of *N. gonorrhoeae*, of approximately 40–55 kD referred to as "NGSP". The invention encompasses an isolated or purified NGSP polypeptide, fragments thereof and polypeptides derived therefrom (NGSP-derived polypeptides), and methods of making thereof. The invention also encompasses antibodies, including cytotoxic or bactericidal antibodies, that specifically bind the NGSP polypeptide, NGSP-derived polypeptides and/or fragments thereof. The invention further encompasses immunogenic, prophylactic or therapeutic compositions, including vaccines, that comprise NGSP polypeptide, NGSP-derived polypeptides and/or fragments thereof. The invention additionally provides methods of inducing an immune response to *Neisseria gonorrhoeae* in an animal and methods of treating infections in an animal caused by *Neisseria gonorrhoeae*. The invention further provides isolated nucleotide sequences encoding the NGSP polypeptide, NGSP-derived polypeptides and fragments thereof, vectors having said sequences, and host cells containing said vectors.

2. BACKGROUND OF THE INVENTION

Neisseriae are gram-negative diplococci and include but are not limited to *Neisseria ovis, Neisseria lacunata, Neisseria osloensis, Neisseria bovis, Neisseria meningitidis*, and *Neisseria gonorrhoeae* and cause a wide range of infectious diseases.

Although intensely investigated at both the clinical and basic research levels for several decades, *Neisseria gonorrhoeae* remains a sexually transmitted disease (STD) of significant health and economic importance for both the developed as well as the developing world. *N.gonorrhoeae* is the second most common STD in the United States with over 200,000 cases being reported to the Centers for Disease Control and Prevention (CDC) in 1998. Gonococcal infections are usually localized to the mucosal surfaces initially contacted by the pathogen such as the cervix, vagina, urethra, conjunctiva, anorectal area, or the pharyngeal surface and where they can produce a variety of clinical diseases such as cervicitis, urethritis, and conjunctivitis (ophthalmia neonatorum). Acute *N.gonorrhoeae* infections generally elicit classical symptoms and are often accompanied by a purulent lymphocytic discharge at the site of infection. Acute *N.gonorrhoeae* infections can often be treated successfully with appropriate antibiotics many gonococcal infections, in both men and women, remain asymptomatic and can persist for years. While most gonococcal infections remain localized, in some individuals, for reasons yet to be understood, the infection can spread from the primary site of infection and produce a severe disseminated disease such as pelvic inflammatory disease (PID), bacteremia, and arthritis. Besides causing adverse consequences to the urogenital tract, infection with *N.gonorrhoeae* has been shown to facilitate the transmission of the human immunodeficiency virus (HIV).

Fluoroquinolones and broad-spectrum cephalosporins are the most effective antimicrobial agents for the treatment of gonorrhea. However, clinically significant resistance to fluoroquinolones has emerged in *Neisseria gonorrhoeae* and raised concerns regarding the future effectiveness and expense of anti-gonococcal treatment regimens. The development of an effective vaccine that would prevent gonococcal infection and/or significantly reduce the sequelae associated with urogenital infection, especially PID, would provide an attractive and proactive method for combating gonococcal infections. Recent advances in our understanding of gonococcal pathogenesis have provided a foundation for identifying and evaluating antigens, individually and in combination, as potential gonococcal vaccines.

The HtrA protein has been identified as a virulence factor for several bacterial pathogens including, *Yersinia enterocolitica, Brucella abortus*, and *Salmonella typhimurium*. In some but not all organisms HtrA appears to be a stress-responsive protein, possibly contributing to the organisms' survival under oxidative challenge and/or at elevated temperatures. The exact role HtrA plays during the pathogenesis process has not yet been fully defined. Bacteria-host cell interaction and the resulting signal transduction events that are triggered in the pathogen may promote expression of the HtrA protein. The *E. coli* and *N. influenzae* HtrA proteins, including the Hin47 protein described in U.S. Pat. Nos. 5,679,547 and 5,721,115, both of which are incorporated herein by reference in their entireties, have been shown to be serine proteases and possess three relatively conserved domains that house the catalytic residues H, D and S.

HtrA is a virulence factor, having serine protease activity, which has recently been identified as a target for the development of anti-bacterial agents against gram negative bacterial pathogens. (Jones and Hruby, 1998, New targets for antibiotic development: biogenesis of surface adherence structures, DDT Vol. 3(11):495–504; Barrett and Hock, 1998, Two-component signal transduction as a target for microbial anti-infective therapy, *Antimicrobial. Agents and Chemother*. 42(7):1529–1536; Fabret and Hock, 1998, A two-component signal transduction system essential for growth of *Bacillus subtillis*: implications for anti-infective therapy, *J. Bacteriol.*, 180(23):63756382).

Citation or identification of any reference in this section or any other section of this application shall not be construed as an indication that such reference is available as prior art to the present invention.

3. SUMMARY OF THE INVENTION

One object of this invention is to identify and provide a novel and highly conserved protein (referred to hereafter and in the claims as "NGSP") from Neisseria spp., preferably *Neisseria gonorrhoeae, Neisseria ovis, Neisseria lacunata, Neisseria osloensis*, and *Neisseria bovis*. The protein of the present invention has a molecular weight of approximately 40–55 kD, and has limited similarity (~36% identity overall) to the DegP (HtrA) protein of *E. coli* (% identity determined using TBLASTP program (Altschul et al., 1990, J. Molec. Biol. 215:403–10; Altschul et al., 1997, Nuc. Acids Res. 25:3389–3402) with data entered using FASTA format; expect 10 filter default; description 100, alignment) and has not been previously identified in any Neisseria spp. The protein sequence which is another object of this invention has similarity to several DegP/HtrA-like serine proteases from two other bacteria and these sequence homologies have not been previously reported for any Neisseria spp.

The invention is based, in part, on the surprising discovery that *Neisseria gonorrhoeae*, and various strains and cultivars thereof, have a protein, NGSP polypeptide, which is about 40 kD to about 55 kD in molecular weight, preferably about 44 kD to about 53 kD.

The present invention encompasses the NGSP polypeptide of *Neisseria gonorrhoeae* and other Neisseria spp, including but not limited to, *Neisseria ovis, Neisseria lacunata, Neisseria osloensis*, and *Neisseria bovis*, having a molecular weight, as determined from the deduced amino acid sequence, of 40 kD to about 55 kD, in isolated or recombinant form. A homologous protein, NMASP, from *Neisseria meningitidis*, is described and claimed in copending application of Applicants entitled "*Neisseria meningitidis* Polypeptide, Gene Sequence And Uses Thereof" (Application No.: 09/388,089) filed on even date herewith, which is hereby incorporated by reference in its entirety. The present invention encompasses a purified NGSP polypeptide, polypeptides including fragments, derived therefrom (NGSP-derived polypeptides), and methods for making said polypeptide and derived polypeptides. The invention also encompasses antisera and antibodies, including cytoxic or bactercidal antibodies, which bind to and are specific for the NGSP polypeptide, NGSP-derived polypeptides and/or fragments thereof.

The invention further encompasses pharmaceutical compositions including prophylactic or therapeutic compositions and which may be antigenic, preferably immunogenic compositions including vaccines, comprising one or more of said polypeptides, optionally in combination with, fused to or conjugated to one or more other component(s), including a lipid, phospholipid, a carbohydrate including a lipopolysaccharide, any protein(s) novel, or known to those skilled in the art, inactivated whole or attenuated organisms, including but not limited to any Neisseria, Chlamydia, Moraxella, Pseudomonas, Streptococcus or Haemophilus bacteria. The invention further encompasses pharmaceutical compositions including prophylactic or therapeutic compositions, which may be immunogenic compositions including vaccines, comprising one or more of the NGSP polypeptide and NGSP-derived polypeptides and an attenuated or inactivated Neisseria cultivar or an attenuated or inactivated Neisseria cultivar expressing NGSP polypeptide in a greater amount when compared to wild-type Neisseria.

The invention additionally provides methods of inducing an immune response to Neisseria spp. in an animal and methods of treating or preventing an infection caused by Neisseria spp. in an animal. Preferred is *N. gonorrhoeae*.

The invention further provides isolated nucleotide sequences encoding the NGSP polypeptide, NGSP-derived polypeptides, and fragments thereof, vectors having said sequences, host cells containing said vectors, recombinant polypeptides produced therefrom, and pharmaceutical compositions comprising the nucleotide sequences, vectors, or cells.

In other embodiments of the invention there are provided methods for identifying compounds which bind to or otherwise interact with and inhibit or activate an activity of a NGSP peptide or polypeptide or the DNA sequences encoding same of the invention comprising: contacting the DNA or polypeptide to assess the binding or other interaction, such binding or interaction being associated with a binding or interaction of the DNA or polypeptide with the compound and determining whether the compounds binds to or otherwise interacts with and activates or inhibits an activity of the DNA or polypeptide by detecting the presence or absence of a signal generated from the binding or interaction of the compounds with the DNA or polypeptide. In accordance with another aspect of the invention, there are provided NGSP agonist or antagonists, preferably bacteriostatic bacteriocidal agonists or antagonists.

One advantage of this invention is that antibody generated against the newly discovered NGSP polypeptide of the present invention, in an animal host will exhibit bactericidal and/or opsonic activity against many Neisseriae strains and thus confer broad cross-strain protection. Bactericidal and/or opsonic antibody will prevent the bacterium from infecting the host and/or enhance the clearance of the pathogen by the host's immune system. Neisseria antibody bactericidal activity is the principal laboratory test that has been correlated with protection in humans and is the standard assay in the field as being predictive of a vaccine's efficacy against Neisseria infections. Bactericidal antibodies are particularly important for *N.gonorrhoeae* vaccines because there is no natural animal host other than humans and thus there is no relevant predictive animal model of disease.

3.1. DEFINITIONS AND ABBREVIATIONS

| | |
|---|---|
| anti-NGSP = | a polyclonal or monoclonal antibody or antiserum that binds specifically to a NGSP polypeptide or NGSP-derived polypeptide |
| ATCC = | American Type Culture Collection |
| blebs = | naturally occurring outer membrane vesicles of Neisseria |
| antigenic = | capable of binding specifically to antibody or T cell receptors and provoking an immune response |
| immunogenic = | capable of provoking a protective cellular or humoral immune response |
| kD = | kilodaltons |
| N. = | Neisseria spp. and includes but is not limited to, *Neisseria ovis, Neisseria lacunata, Neisseria osloensis, Neisseria bovis*, and *Neisseria gonorrhoeae* |
| NGSP = | a non-cytosolic polypeptide of a Neisseria spp. particularly *N. gonorrhoeae*, or any strain or cultivar thereof, having a molecular weight of about 40 kD to 55 kD; |
| NGSP-derived polypeptide = | fragment of the NGSP polypeptide; variant of wild-type NGSP polypeptide or fragment thereof, containing one or more amino acid deletions, insertions or substitutions; or chimeric protein comprising a heterologous polypeptide fused to a C-terminal or N-terminal or internal segment of a whole or a portion of the NGSP polypeptide; |
| OG = | n-octyl-β-D-glucopyranoside or octylglucoside |
| PBS = | phosphate buffered saline |
| PAG = | polyacrylamide gel |
| polypeptide = | a peptide or protein of any length, preferably one having eight or more amino acid residues |
| SDS = | sodium dodecylsulfate |
| SDS-PAGE = | sodium dodecylsulfate polyacrylamide gel electrophoresis |

Nucleotide or nucleic acid sequences defined herein are represented by one-letter symbols for the bases as follows:

A (adenine)
C (cytosine)
G (guanine)
T (thymine)
U (uracil)
M (A or C)
R (A or G)
W (A or T/U)
S (C or G)
Y (C or T/U)
K (G or T/U)
V (A or C or G; not T/U)
H (A or C or T/U; not G)

D (A or G or T/U; not C)
B (C or G or T/U; not A)
N (A or C or G or T/U) or (unknown)

Peptide and polypeptide sequences defined herein are represented by one-letter or three symbols for amino acid residues as follows:

| 1 letter | 3 letter | amino acid |
|---|---|---|
| A | Ala | (alanine) |
| R | Arg | (arginine) |
| N | Asn | (asparagine) |
| D | Asp | (aspartic acid) |
| C | Cys | (cysteine) |
| Q | Gln | (glutamine) |
| E | Glu | (glutamic acid) |
| G | Gly | (glycine) |
| H | His | (histidine) |
| I | Ile | (isoleucine) |
| L | Leu | (leucine) |
| K | Lys | (lysine) |
| M | Met | (methionine) |
| F | Phe | (phenylalanine) |
| P | Pro | (proline) |
| S | Ser | (serine) |
| T | Thr | (threonine) |
| W | Trp | (tryptophan) |
| Y | Tyr | (tyrosine) |
| V | Val | (valine) |
| X | Xaa | (unknown) |

The present invention may be more fully understood by reference to the following detailed description of the invention, non-limiting examples of specific embodiments of the invention and the appended figures.

4. BRIEF DESCRIPTION OF THE FIGURES

FIG. 1: Map of NGSP vector pTLZ-NgHtrA#2.

Figure 2:
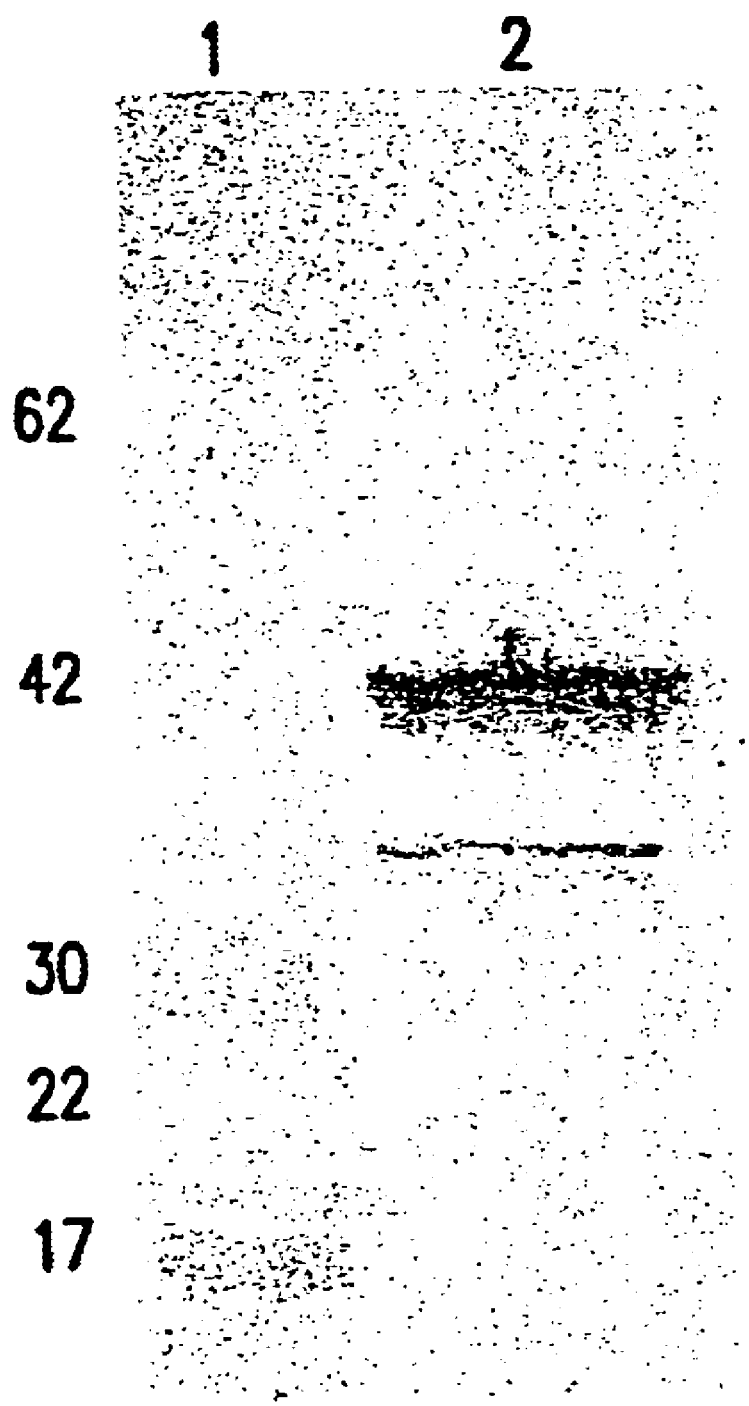

FIG. 2: Western blot of NGSP protein (lane 2) expressed from IPTG induced JM109 (pTLZ-NgHtrA#2). A monoclonal anti-(His)$_5$ antibody conjugated to HRP (QiaGen) was used to identify the protein and visualization of the antibody reactive pattern was achieved on Hyperfilm using the Amersham ECL chemiluminescence system. Lane 1 shows Novex MultiMark molecular weight markers of glutamic dehydrogenase (62 kD), carbonic anhydrase (42 kD), myoglobin-blue (30 kD), myoglobin-red (22 kD), and lysozyme(17 kD).

5. DETAILED DESCRIPTION OF THE INVENTION

5.1. NGSP Polypeptide

The invention provides an isolated or a substantially pure native (wild type) or recombinantly produced polypeptide, referred to as NGSP, of Neisseria spp. including but not limited to, *Neisseria ovis, Neisseria lacunata, Neisseria osloensis, Neisseria bovis*, and *Neisseria gonorrhoeae*, and various strains or cultivars thereof, but not of *Neisseria meningitidis*. The NGSP polypeptide comprises the whole or a subunit of a non-cytosolic protein embedded in, or located in the bacterial envelope, which may include the inner membrane, outer surface, and periplasmic space. The NGSP polypeptide has an apparent molecular weight, as determined from the deduced amino acid sequence, of about 40 kD to about 55 kD, preferably about 44 kD to about 53 kD.

NGSP polypeptide may also be identified as the polypeptide in hydrophobic (salt) or detergent extracts of Neisseria blebs or intact cells that has an apparent molecular weight about 40 kD to about 55 kD, preferably about 44 kD to about 53 kD, as determined by denaturing gel electrophoresis in 12% PAG with SDS, using formulations as described in Harlow and Lane (*Antibodies: A Laboratory Manual*, Cold Spring Harbor Laboratory Press, Cold Spring Harbor, NY, Appendix I, 1988).

In particular embodiments, the NGSP polypeptide is that obtainable from any of *Neisseria gonorrhoeae, Neisseria ovis, Neisseria lacunata, Neisseria osloensis*, and *Neisseria bovis*. Preferred species are *Neisseria gonorrhoeae*. Strains from any of these organisms may be obtained worldwide from any biologicals depository, particularly strains of N.g. ATCC 9793, ATCC 9827, ATCC 9828, ATCC 9830, ATCC 10150, ATCC 10874, ATCC 11688, ATCC 11689, ATCC 19088, ATCC 19424, ATCC 21823, ATCC 21824, ATCC 21825, ATCC 23050, ATCC 23051, ATCC 27628, ATCC 27629, ATCC 27630, ATCC 27631, ATCC 27632, ATCC 27633, ATCC 31148, ATCC 31149, ATCC 31150, ATCC 31151, ATCC 31356, ATCC 31397, ATCC 31398, ATCC 31399, ATCC 31400, ATCC 31401, ATCC 31402, ATCC 31403, ATCC 31404, ATCC 31405, ATCC 31406, ATCC 31407, ATCC 31426, ATCC 31953, ATCC 33084, ATCC 35201, ATCC 35541, ATCC 35542, ATCC 43069, ATCC 43070, ATCC 43785, ATCC 49226, ATCC 49498, ATCC 49759, ATCC 49926, ATCC 49981, ATCC 51109, ATCC 51803, ATCC 51804, ATCC 53420, ATCC 53421, ATCC 53422, ATCC 53423, ATCC 53424, and ATCC 53425.

In a particular embodiment, the NGSP polypeptide comprises a deduced amino acid sequence as depicted in SEQ ID NO: 4. Particularly preferred fragments of NGSP have deduced amino acid sequences depicted in SEQ ID NOs: 6, 7, 9 and 10. In another particular embodiment, the NGSP polypeptide is encoded by the nucleotide sequence of SEQ ID NOs: 3 or 5, with particularly preferred fragments encoded by nucleotide sequences depicted in SEQ ID NOs: 1, 2 and 7. In another embodiment, the NGSP polypeptide comprises an amino acid sequence which is substantially homologous to the deduced amino acid sequence of SEQ ID NO: 4 or a portion thereof or is encoded by a nucleotide sequence substantially homologous to the nucleotide sequence of SEQ ID No: 3 or 5 or a portion thereof.

As used herein a "substantially homologous" sequence is at least 70%, preferably greater than 80%, more preferably greater than 90% identical to a reference sequence of identical size or when compared to a reference sequence when the alignment or comparison is conducted by a computer homology program or search algorithm known in the art. By way of example and not limitation, useful computer homology programs include the following: Basic Local Alignment Search Tool (BLAST) (Altschul et al., 1990, *J. of Molec. Biol.*, 215:403–410, "The BLAST Algorithm; Altschul et al., 1997, *Nuc. Acids Res.* 25:3389–3402) a heuristic search algorithm tailored to searching for sequence similarity which ascribes significance using the statistical methods of Karlin and Altschul 1990, *Proc. Nat'l Acad. Sci. USA*, 87:2264–68; 1993, *Proc. Nat'l Acad. Sci. USA* 90:5873–77. Five specific BLAST programs perform the following tasks:

1) The BLASTP program compares an amino acid query sequence against a protein sequence database.

2) The BLASTN program compares a nucleotide query sequence against a nucleotide sequence database.

3) The BLASTX program compares the six-frame conceptual translation products of a nucleotide query sequence (both strands) against a protein sequence database.

4) The TBLASTN program compares a protein query sequence against a nucleotide sequence database translated in all six reading frames (both strands).

5) The TBLASTX program compares the six-frame translations of a nucleotide query sequence against the six-frame translations of a nucleotide sequence database.

Smith-Waterman (database: European Bioinformatics Institute (Smith-Waterman, 1981, *J. of Molec. Biol.*, 147:195–197) is a mathematically rigorous algorithm for sequence alignments.

FASTA (see Pearson et al., 1988, *Proc. Nat'l Acad. Sci. USA*, 85:2444–2448) is a heuristic approximation to the Smith-Waterman algorithm. For a general discussion of the procedure and benefits of the BLAST, Smith-Waterman and FASTA algorithms see Nicholas et al., 1998, "A Tutorial on Searching Sequence Databases and Sequence Scoring Methods" and references cited therein.

By further way of example and not limitation, useful computer homology algorithms and parameters for determining percent identity include the following:

To determine the percent identity of two amino acid sequences or of two nucleic acids, e.g. between Thy-1 sequences and other known sequences, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment, the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul, 1990, Proc. Natl. Acad. Sci. USA 87:2264–2268, modified as in Karlin and Altschul, 1993, Proc. Natl. Acad. Sci. USA 90:5873–5877. Such an algorithm is incorporated into the NBLAST and XBLAST programs of Altschul, et al., 1990, J. Mol. Biol. 215:403–410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al., 1997, Nucleic Acids Res. 25:3389–3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the CGC sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti (1994) Comput. Appl. Biosci., 10:3–5; and FASTA described in Pearson and Lipman (1988) Proc. Natl. Acad. Sci. 85:2444–8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA.

Alternatively, protein sequence alignment may be carried out using the CLUSTAL W algorithm, as described by Higgins et al., 1996, Methods Enzymol. 266:383–402.

The percent identity between two sequences can be determined using techniques similar to those described above, with or without allowing gaps. In calculating percent identity, only exact matches are counted.

According to various aspects of the invention, the polypeptides of the invention are characterized by their apparent molecular weights based on the polypeptides' migration in SDS-PAGE relative to the migration of known molecular weight markers. While any molecular weight standards known in the art may be used with the SDS-PAGE, preferred molecular weight markers comprise at least glutamic dehydrogenase and carbonic anhydrase. Other markers include bovine serum albumin, chicken ovalbumin and bovine carbonic anhydrase. One skilled in the art will appreciate that the polypeptides of the invention may migrate differently in different types of gel systems (e.g., different buffers; different types and concentrations of gel, crosslinkers or SDS, etc.). One skilled in the art will also appreciate that the polypeptides may have different apparent molecular weights due to different molecular weight markers used with the SDS-PAGE. Hence, the molecular weight characterization of the polypeptides of the invention is intended to be directed to cover the same polypeptides on any SDS-PAGE systems and with any molecular weight markers which might indicate sightly different apparent molecular weights for the polypeptides than those disclosed herein.

5.2. NGSP-derived Polypeptides

An NGSP-derived polypeptide of the invention may be a fragment of the NGSP polypeptide. Fragments include those polypeptides having 7 or more amino acids; preferably 8 or more amino acids; more preferably 9 or more amino acids; and most preferably 10 or more amino acids of the NGSP polypeptide.

The intact NGSP polypeptide may contain one or more amino acid residues that are not necessary to its immunogenicity. It may be the case, for example, that only the amino acid residues forming a particular epitope of the NGSP polypeptide are necessary for immunogenic activity. Unnecessary amino acid sequences can be removed or modified by techniques well known in the art, i.e., an NGSP-derived polypeptide.

Preferably, the NGSP-derived polypeptides of the invention are antigenic, i.e., binding specifically to an anti-NGSP antibody and more preferably, the NGSP-derived polypeptides are immunogenic and immunologically cross-reactive with the NGSP polypeptide, thus being capable of eliciting in an animal an immune response to Neisseria. More preferably, the NGSP-derived polypeptides of the invention comprise sequences forming one or more epitopes of the native NGSP polypeptide of Neisseria (i.e., the epitopes of NGSP polypeptide as it exists in intact Neisseria cells). Such preferred NGSP-derived polypeptides can be identified by their ability to specifically bind antibodies raised to intact Neisseria cells (e.g., antibodies elicited by formaldehyde or glutaraldehyde fixed Neisseria cells; such antibodies are referred to herein as "anti-whole cell" antibodies). For example, polypeptides or peptides from a limited or complete protease digestion of the NGSP polypeptide are fractionated using standard methods and tested for their ability to bind anti-whole cell antibodies. Reactive polypeptides comprise preferred NGSP-derived polypeptides. They are isolated and their amino acid sequences determined by methods known in the art.

Also preferably, the NGSP-derived polypeptides of the invention comprise sequences that form one or more epitopes of native NGSP polypeptide that mediate bactericidal or opsonizing antibodies. Such preferred NGSP-derived polypeptides may be identified by their ability to generate antibodies that kill Neisseria spp., particularly, N. gonorrhoeae cells. For example, polypeptides from a limited or complete protease digestion or chemical cleavage of NGSP polypeptide are fractionated using standard methods, injected into animals and the antibodies produced therefrom tested for the ability to interfere with or kill Neisseria cells. Once identified and isolated, the amino acid sequences of such preferred NGSP-derived polypeptides are determined using standard sequencing methods. The determined sequence may be used to enable production of such polypeptides by synthetic chemical and/or genetic engineering means.

These preferred NGSP-derived polypeptides also can be identified by using anti-whole cell antibodies to screen bacterial libraries expressing random fragments of Neisseria genomic DNA or cloned nucleotide sequences encoding the whole NGSP polypeptide or fragments thereof. See, e.g., Sambrook et al., Molecular Cloning, A Laboratory Manual, 2nd ed., Cold Spring Harbor Press, N.Y., Vol. 1, Chapter 12. The reactive clones are identified and their inserts are isolated and sequenced to determine the amino acid sequences of such preferred NGSP-derived polypeptides.

By way of example and not limitation, the unwanted amino acid sequences can be removed or modified by limited proteolytic digestion using enzymes such as trypsin, papain, or related proteolytic enzymes or by chemical cleavage using agents such as cyanogen bromide and followed by fractionation of the digestion or cleavage products.

An NGSP-derived polypeptide of the invention may also be a modified NGSP polypeptide or fragment thereof (i.e., an NGSP polypeptide or fragment having one or more amino acid substitutions, insertions and/or deletions of the wild-type NGSP sequence or amino acids chemically modified in vivo or in vitro). Such modifications may enhance the immunogenicity of the resultant polypeptide product or have no effect on such activity. The NGSP-derived polypeptides maintain specific binding activity to anti-NGSP. Modification techniques that may be used include those disclosed in U.S. Pat. No. 4,526,716.

As an illustrative, non-limiting example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

An NGSP-derived polypeptide of the invention may also be a molecule comprising a region that is substantially homologous to (e.g., in various embodiments, at least 60% or 70% or 80% or 90% or 95% identity over an amino acid sequence of identical size or when compared to an aligned sequence in which the alignment is performed by a computer homology program known in the art) or whose encoding nucleic acid is capable of hybridizing to a coding NGSP sequence, under highly stringent, moderately stringent, or low or nonstringent conditions.

By way of example and not limitation, useful computer homology programs include the following: Basic Local Alignment Search Tool (BLAST) (Altschul et al., 1990, *J. of Molec. Biol.*, 215:403–410, "The BLAST Algorithm; Altschul et al., 1997, *Nuc. Acids Res.* 25:3389–3402) a heuristic search algorithm tailored to searching for sequence similarity which ascribes significance using the statistical methods of Karlin and Altschul (1990, *Proc. Nat'l Acad. Sci. USA*, 87:2264–68; 1993, *Proc. Nat'l Acad. Sci. USA* 90:5873–77). Two specific BLAST programs perform the following tasks:
1) The BLASTP program compares an amino acid query sequence against a protein sequence database; and
2) The BLASTN program compares a nucleotide query sequence against a nucleotide sequence database; and hence are useful to identify, respective substantially homologous amino acid and nucleotide sequences.

Additional algorithms which can be useful are the Smith-Waterman and FASTA algorithms. See sup& Section 5.1 for a more detailed description description of useful algorithms and parameters for determining percent identity of nucleotide (and/or amino acid) sequences.

Included within the scope of the invention are NGSP-derived polypeptides which are NGSP polypeptide fragments or other derivatives or analogs which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

Furthermore, if desired, nonclassical amino acids or chemical amino acid analogs can be introduced as a substitution or addition into the NGSP polypeptide sequence. Non-classical amino acids include but are not limited to the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, pbenylglycine, cyclobexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

An NGSP-derived polypeptide may further be a chimeric polypeptide comprising one or more heterologous polypeptides, lipids, phospholipids or lipopolysaccharides of Neisserial origin or of another bacterial origin, fused to the amino-terminal or carboxyl-terminal or internal of a complete NGSP polypeptide or a portion of or a fragment thereof. Useful heterologous polypeptides comprising such chimeric polypeptide include, but are not limited to, a) pre- and/or pro- sequences that facilitate the transport, translocation and/or processing of the NGSP-derived polypeptide in a host cell, b) affinity purification sequences, and c) any useful immunogenic sequences (e.g., sequences encoding one or more epitopes of a surface-exposed protein of a microbial pathogen). One preferred heterologous protein of the chimeric polypeptide of the invention includes Hin47 (see U.S. Pat. Nos. 5,679,547 and 5,721,115).

5.3. Isolation and Purification of NGSP Polypeptide and NGSP-derived Polypeptides The invention provides isolated NGSP polypeptides and NGSP-derived polypeptides. As used herein, the term "isolated" means that the product is significantly free of other biological materials with which it is naturally associated. That is, for example, an isolated NGSP polypeptide composition is between about 70% and 94% pure NGSP polypeptide by weight. Preferably, the NGSP polypeptides and NGSP-derived polypeptides of the invention are purified. As used herein, the term "purified" means that the product is substantially free of other biological material with which it is naturally associated. That is, a purified NGSP polypeptide composition is at least 95% pure NGSP polypeptide by weight, preferably at least 98% pure NGSP polypeptide by weight, and most preferably at least 99% pure NGSP polypeptide by weight.

The NGSP polypeptide of the invention may be isolated from a protein extract including a whole cell extract, of any Neisseria spp., including, but not limited to, *Neisseria ovis, Neisseria lacunata, Neisseria osloensis, Neisseria bovis,* and *Neisseria gonorrhoeae* (N.g). Preferred species are N.g. Strains from any of these organisms may be obtained worldwide from any biologicals depository, particularly strains of N.g. ATCC 9793, ATCC 9827, ATCC 9828, ATCC 9830, ATCC 10150, ATCC 10874, ATCC 11688, ATCC 11689, ATCC 19088, ATCC 19424, ATCC 21823, ATCC 21824, ATCC 21825, ATCC 23050, ATCC 23051, ATCC 27628, ATCC 27629, ATCC 27630, ATCC 27631, ATCC 27632, ATCC 27633, ATCC 31148, ATCC 31149, ATCC 31150, ATCC 31151, ATCC 31356, ATCC 31397, ATCC 31398, ATCC 31399, ATCC 31400, ATCC 31401, ATCC 31402, ATCC 31403, ATCC 31404, ATCC 31405, ATCC 31406, ATCC 31407, ATCC 31426, ATCC 31953, ATCC 33084, ATCC 35201, ATCC 35541, ATCC 35542, ATCC 43069, ATCC 43070, ATCC 43785, ATCC 49226, ATCC 49498, ATCC 49759, ATCC 49926, ATCC 49981, ATCC 51109, ATCC 51803, ATCC 51804, ATCC 53420, ATCC 53421, ATCC 53422, ATCC 53423, ATCC 53424, and ATCC 53425. Another source of the NGSP polypeptide is a protein preparation from a gene expression system expressing a sequence encoding NGSP polypeptide or NGSP-derived polypeptides (see Section 5.7., infra).

The NGSP polypeptide can be isolated and purified from the source material using any biochemical technique and approach well known to those skilled in the art. In one approach, Neisseria cellular envelope is obtained by standard techniques and inner membrane, periplasmic and outer membrane proteins are solubilized using a solubilizing agent such as a detergent or hypotonic solution. A preferred detergent solution is one containing octyl glucopyranoside (OG), sarkosyl or TRITON X100™ (t-octylphenoxypolyethoxyethanol). A preferred solubilizing hypotonic solution is one containing LiCl. NGSP polypeptide is in the solubilized fraction. Cellular debris and insoluble material in the extract are separated and removed preferably by centrifuging. The polypeptides in the extract are concentrated, incubated in SDS-containing Laemmli gel sample buffer at 100° C. for 5 minutes and then fractionated by electrophoresis in a denaturing sodium dodecylsulfate (SDS) polyacrylamide gel (PAG) from about 6% to about 12%, with or without a reducing agent. See Laemmli, 1970, Nature 227:680–685. The band or fraction identified as NGSP polypeptide, having an apparent molecular weight of about 40 kD to about 55 kD, as described above, may then be isolated directly from the fraction or gel slice containing the NGSP polypeptide. In a preferred embodiment, NGSP polypeptide has an apparent molecular weight of about 44 kD to about 53 kD which could be determined by comparing its migration distance or rate in a denaturing SDS-PAGE relative to those of bovine serum albumin (66.2 kD) and chicken ovalbumin (45 kD).

Another method of purifying NGSP polypeptide is by affinity chromatography using anti-NGSP antibodies, (see Section 5.5). Preferably, monoclonal anti-NGSP antibodies are used. The antibodies are covalently linked to agarose gels activated by cyanogen bromide or succinamide esters (Affi-Gel, BioRad, Inc.) or by other methods known to those skilled in the art. The protein extract is loaded on the top of the gel as described above. The contact is for a period of time and under standard reaction conditions sufficient for NGSP polypeptide to bind to the antibody. Preferably, the solid support is a material used in a chromatographic column. NGSP polypeptide is then removed from the antibody, thereby permitting the recovery NGSP polypeptide in isolated, or preferably, purified form.

An NGSP-derived polypeptide of the invention can be produced by chemical and/or enzymatic cleavage or degradation of isolated or purified NGSP polypeptide. An NGSP-derived polypeptide can also be chemically synthesized based on the known amino acid sequence of NGSP polypeptide and, in the case of a chimeric polypeptide, the amino acid sequence of the heterologous polypeptide by methods well known in the art. See, for example, Creighton, 1983, Proteins: Structures and Molecular Principles, W. H. Freeman and Co., NY.

An NGSP-derived polypeptide can also be produced in a gene expression system expressing a recombinant nucleotide construct comprising a sequence encoding NGSP-derived polypeptides. The nucleotide sequences encoding polypeptides of the invention may be synthesized, and/or cloned, and expressed according to techniques well known to those skilled in the art. See, for example, Sambrook, et al., 1989, Molecular Cloning, A Laboratory Manual, Vols. 1–3, Cold Spring Harbor Press, NY, Chapter 9.

NGSP-derived polypeptides of the invention can be fractionated and purified by the application of standard protein purification techniques, modified and applied in accordance with the discoveries and teachings described herein. In particular, preferred NGSP-polypeptides of the invention, those that form an outer-surface or exposed epitope of the native NGSP polypeptide may be isolated and purified according to the affinity procedures disclosed above for the isolation and purification of NGSP polypeptide (e.g., affinity purification using anti-NGSP antibodies).

If desirable, the polypeptides of the invention may be further purified using standard protein or peptide purification techniques including but not limited to electrophoresis, centrifugation, gel filtration, precipitation, dialysis, chromatography (including ion exchange chromatography, affinity chromatography, immunoadsorbent affinity chromatography, reverse-phase high performance liquid chromatography, and gel permeation high performance liquid chromatography), isoelectric focusing, and variations and combinations thereof.

One or more of these techniques may be employed sequentially in a procedure designed to isolate and/or purify the NGSP polypeptide or the NMAP-derived polypeptides of the invention according to its/their physical or chemical characteristics. These characteristics include the hydrophobicity, charge, binding capability, and molecular weight of the protein. The various fractions of materials obtained after each technique are tested for their abilities to bind the NGSP receptor or ligand, to bind anti-NGSP antibodies or to have serine protease activity ("test" activities). Those fractions showing such activity are then subjected to the next technique in the sequential procedure, and the new fractions are tested again. The process is repeated until only one fraction having the above described "test" activities remains and that fraction produces only a single band or entity when subjected to polyacrylamide gel electrophoresis or chromatography.

5.4. NGSP Immunogens and Anti-NGSP Antibodies

The present invention provides antibodies that specifically bind NGSP polypeptide or NGSP-derived polypeptides. For the production of such antibodies, isolated or preferably, purified preparations of NGSP polypeptide or NGSP-derived polypeptides are used as antigens in an antigenic composition, more preferably as immunogens in an immunogenic composition.

In an embodiment, the NGSP polypeptide is separated from other outer membrane or periplasmic proteins present in the extracts of Neisseria cells or blebs using SDS-PAGE (see Section 5.3. above) and the gel slice containing NGSP polypeptide is used as an immunogen and injected into a rabbit to produce antisera containing polyclonal NGSP antibodies. The same immunogen can be used to immunize mice for the production of hybridoma lines that produce monoclonal anti-NGSP antibodies. In particular embodiments, the immunogen is a PAGE slice containing isolated or purified NGSP from any *Neisseria gonorrhoeae*, including, but not limited to, *Neisseria ovis, Neisseria lacunata, Neisseria osloensis, Neisseria bovis*, and *Neisseria gonorrhoeae* (Ng). Preferred species are N.g. Particularly preferred are the strains of N.g. ATCC 9793, ATCC 9827, ATCC 9828, ATCC 9830, ATCC 10150, ATCC 10874, ATCC 11688, ATCC 11689, ATCC 19088, ATCC 19424, ATCC 21823, ATCC 21824, ATCC 21825, ATCC 23050, ATCC 23051, ATCC 27628, ATCC 27629, ATCC 27630, ATCC 27631, ATCC 27632, ATCC 27633, ATCC 31148, ATCC 31149, ATCC 31150, ATCC 31151, ATCC 31356, ATCC 31397, ATCC 31398, ATCC 31399, ATCC 31400, ATCC 31401, ATCC 31402, ATCC 31403, ATCC 31404, ATCC 31405, ATCC 31406, ATCC 31407, ATCC 31426, ATCC 31953, ATCC 33084, ATCC 35201, ATCC 35541, ATCC 35542, ATCC 43069, ATCC 43070, ATCC 43785, ATCC 49226, ATCC 49498, ATCC 49759, ATCC 49926, ATCC 49981, ATCC 51109, ATCC 51803, ATCC 51804, ATCC 53420, ATCC 53421, ATCC 53422, ATCC 53423, ATCC 53424, and ATCC 53425.

In other embodiments, peptide fragments of NGSP polypeptide are used as immunogens. Preferably, peptide fragments of purified NGSP polypeptide are used. The peptides may be produced by protease digestion, chemical cleavage of isolated or purified NGSP polypeptide or chemical synthesis and then may be isolated or purified. Such isolated or purified peptides can be used directly as immunogens. In particular embodiments, useful peptide fragments are 5 or more amino acids in length.

Useful immunogens may also comprise such peptides or peptide fragments conjugated to a carrier molecule, preferably a carrier protein. Carrier proteins may be any commonly used in immunology, include, but are not limited to, bovine serum albumin (BSA), chicken albumin, keyhole limpet hemocyanin (KLH) and the like. For a discussion of hapten protein conjugates, see, for example, Hartlow, et al., *Antibodies: A Laboratory Manual*, Cold Spring Harbor Laboratory Press, Cold Spring Harbor, N.Y., 1988, or a standard immunology textbook such as Roitt, I. et al., *IMMUNOLOGY*, C. V. Mosby Co., St. Louis, Mo. (1985) or Klein, J., *IMMUNOLOGY*, Blackwell Scientific Publications, Inc., Cambridge, Mass., (1990).

In yet another embodiment, for the production of antibodies that specifically bind one or more epitopes of the native NGSP polypeptide, intact Neisseria cells or blebs prepared therefrom are used as immunogen. The cells or blebs may be fixed with agents such as formaldehyde or glutaraldehyde before immunization. See Harlow and Lane, *Antibodies: A Laboratory Manual*, Cold Spring Harbor Laboratory Press, Cold Spring Harbor, N.Y., 1988, Chapter 15. It is preferred that such anti-whole cell antibodies be monoclonal antibodies. Hybridoma lines producing the desired monoclonal antibodies can be identified by using purified NGSP polypeptide as the screening ligand. The immunogen for inducing these antibodies are whole cells, blebs, extracts or lysates of any Neisseria, including, but not limited to, *Neisseria ovis, Neisseria lacunata, Neisseria osloensis, Neisseria bovis*, and *Neisseria gonorrhoeae* (N.g.). Preferred species are N.g. Particularly preferred are strains of N.g. ATCC 9793, ATCC 9827, ATCC 9828, ATCC 9830, ATCC 10150, ATCC 10874, ATCC 11688, ATCC 11689, ATCC 19088, ATCC 19424, ATCC 21823, ATCC 21824, ATCC 21825, ATCC 23050, ATCC 23051, ATCC 27628, ATCC 27629, ATCC 27630, ATCC 27631, ATCC 27632, ATCC 27633, ATCC 31148, ATCC 31149, ATCC 31150, ATCC 31151, ATCC 31356, ATCC 31397, ATCC 31398, ATCC 31399, ATCC 31400, ATCC 31401, ATCC 31402, ATCC 31403, ATCC 31404, ATCC 31405, ATCC 31406, ATCC 31407, ATCC 31426, ATCC 31953, ATCC 33084, ATCC 35201, ATCC 35541, ATCC 35542, ATCC 43069, ATCC 43070, ATCC 43785, ATCC 49226, ATCC 49498, ATCC 49759, ATCC 49926, ATCC 49981, ATCC 51109, ATCC 51803, ATCC 51804, ATCC 53420, ATCC 53421, ATCC 53422, ATCC 53423, ATCC 53424, and ATCC 53425.

Polyclonal antibodies produced by whole cell or bleb immunizations contain antibodies that bind other Neisseria proteins ("non-anti-NGSP antibodies") and thus are more cumbersome to use where it is known or suspected that the sample contains other Neisseria proteins or materials that are cross-reactive with these other proteins. Under such circumstances, any binding by the anti-whole cell antibodies of a given sample or band must be verified by coincidental binding of the same sample or band by antibodies that specifically bind NGSP polypeptide (e.g., anti-NGSP) and/or a NGSP-derived polypeptide, or by competition tests using anti-NGSP antibodies, NGSP polypeptide or NGSP-derived polypeptide as the competitor (i.e., addition of anti-NGSP antibodies, NGSP polypeptide or NGSP-derived polypeptide to the reaction mix lowers or abolishes sample binding by anti-whole cell antibodies). Alternatively, such polyclonal antisera, containing "non-anti-NGSP" antibodies, may be cleared of such antibodies by standard approaches and methods. For example, the non-anti-NGSP antibodies may be removed by precipitation with cells of a NGSP deletion or "knockout" mutant Neisseria cultivars or Neisseria strains known not to have the NGSP polypeptide; or by absorption to columns comprising such cells or outer membrane proteins of such cells.

In further embodiments, useful immunogens for eliciting antibodies of the invention comprise mixtures of two or more of any of the above-mentioned individual immunogens.

Immunization of animals with the immunogens described herein, preferably humans, rabbits, rats, mice, sheep, goats, cows or horses, is performed following procedures well known to those skilled in the art, for purposes of obtaining antisera containing polyclonal antibodies or hybridoma lines secreting monoclonal antibodies.

Monoclonal antibodies can be prepared by standard techniques, given the teachings contained herein. Such techniques are disclosed, for example, in U.S. Pat. No. 4,271,145 and U.S. Pat. No. 4,196,265. Briefly, an animal is immunized with the immunogen. Hybridomas are prepared by fusing spleen cells from the immunized animal with myeloma cells. The fusion products are screened for those producing antibodies that bind to the immunogen. The positive hybridomas clones are isolated, and the monoclonal antibodies are recovered from those clones.

Immunization regimens for production of both polyclonal and monoclonal antibodies arc well known in the art. The immunogen may be injected by any of a number of routes, including subcutaneous, intravenous, intraperitoneal, intradermal, intramuscular, mucosal, or a combination of these. The immunogen may be injected in soluble form, aggregate form, attached to a physical carrier, or mixed with an adjuvant, using methods and materials well known in the art. The antisera and antibodies may be purified using column chromatography methods well known to those of skill in the art.

According to the present invention, NGSP polypeptides of Neisseria strains are immnuno-cross reactive. Thus, antibodies raised to NGSP polypeptide of one Neisseria species, strain or cultivar, specifically bind NGSP polypeptide and NGSP-derived polypeptides of other Neisseria species, strains and cultivars. For example, polyclonal anti-NGSP antibodies induced by NGSP polypeptide of N.g. specifically bind not only the identical strain NGSP polypeptide (i.e., the NGSP polypeptide of Nag.) but also NGSP polypeptide and/or NGSP-derived polypeptides of other Neisseria, including, but not limited to, *Neisseria ovis, Neisseria lacunata, Neisseria osloensis, Neisseria bovis, Neisseria meningitidis*, and *Neisseria gonorrhoeae* (Nag.). Preferred species are N.g.

The antibodies of the invention, including but not limited to anti-NGSP antibodies, can be used to facilitate isolation and purification of NGSP polypeptide and NGSP-derived polypeptides. The antibodies may also be used as probes for identifying clones in expression libraries that have inserts encoding NGSP polypeptide or fragments thereof The antibodies may also be used in immunoassays (e.g., ELISA, RIA, Westerns) to specifically detect and/or quantitate Neisseria in biological specimens. Anti-NGSP antibodies of the invention specifically bind NGSP polypeptide from Neisseria, including, but not limited to, *Neisseria ovis, Neisseria lacunata, Neisseria osloensis, Neisseria bovis, Neisseria meningitidis*, and *Neisseria gonorrhoeae*. Thus anti-NGSP antibodies can be used to diagnose Neisseria infections.

The antibodies of the invention, particularly those which are cytotoxic, may also be used in passive immunization to prevent or attenuate Neisseria infections of animals, including humans. (As used herein, a cytotoxic antibody is one which enhances opsonization and/or complement killing of the bacterium bound by the antibody). An effective concentration of polyclonal or monoclonal antibodies raised against the immunogens of the invention may be administered to a host to achieve such effects. The exact concentration of the antibodies administered will vary according to each specific antibody preparation, but may be determined using standard techniques well known to those of ordinary skill in the art. Administration of the antibodies may be accomplished using a variety of techniques, including, but not limited to those described in Section 5.6. for the delivery of vaccines.

5.5. Compositions

The present invention also provides therapeutic and prophylactic compositions, which may be immunogenic compositions including vaccines, against Neisseria infections of animals, including mammals, and more specifically rodents and primates, including humans. Preferred immunogenic compositions include vaccines for use in humans. The immunogenic compositions of the present invention can be prepared by techniques known to those skilled in the art and would comprise, for example, an immunologically effective amount of any of the NGSP immunogens disclosed in Section 5.4., optionally in combination with or fused to or conjugated to one or more other imunungens, including lipids, phospholipids, carbohydrates, lipopolysaccharides, inactivated or attenuated whole organisms and other proteins, of Neisserial origin or other bacterial origin, a pharmaceutically acceptable carrier, optionally an appropriate adjuvant, and optionally other materials traditionally found in vaccines. Such a cocktail vaccine (comprising several immunogens) has the advantage that immunity against one or several pathogens can be obtained by a single administration. Examples of other immunogens include, but are not limited to, those used in the known DPT vaccines, entire organisms or subunits therefrom of Chlamydia, HIV, *Haemophilus influenzae, Moraxella catarrhalis*, and *Streptococcus pneumoniae*, etc.

The term "immunologically effective amount" is used herein to mean an amount sufficient to induce an immune response to produce antibodies, in the case of a humoral immune response, and/or cytokines and other cellular immune response components. Preferably, the immunogenic composition is one that prevents Neisseria infections or attenuates the severity of any preexisting or subsequent Neisseria infection. An immunologically effective amount of the immunogen to be used in the vaccine is determined by means known in the art in view of the teachings herein. The exact concentration will depend upon the specific immunogen to be administered, but can be determined by using standard techniques well known to those skilled in the art for assaying the development of an immune response.

The combined immunogen and carrier or diluent may be an aqueous solution, emulsion or suspension or may be a dried preparation. In general, the quantity of polypeptide immunogen will be between 0.1 and 500 micrograms per dose. The carriers are known to those skilled in the art and include stabilizers, diluents, and buffers. Suitable stabilizers include carbohydrates, such as sorbitol, lactose, mannitol, starch, sucrose, dextran, and glucose and proteins, such as albumin or casein. Suitable diluents include saline, Hanks Balanced Salts, and Ringers solution. Suitable buffers include an alkali metal phosphate, an alkali metal carbonate, or an alkaline earth metal carbonate.

The immunogenic compositions, including vaccines, may also contain one or more adjuvant or immunostimulatory compounds to improve or enhance the immunological response. Suitable adjuvants include, but are not limited to, peptides including bacterial toxins, such as but not limited to heat labile toxin and/or verotoxin of *E. coli*, cholera toxin, and shiga toxin and toxoids and/or attenuated forms thereof, chemokines, cytokines and the like; aluminum hydroxide; aluminum phosphate; aluminum oxide; a composition that consists of a mineral oil, such as Marcol 52, or a vegetable oil, and one or more emulsifying agents or surface active substances such as saponins, lysolecithin, polycations, polyanions; and potentially useful human adjuvants such as BCG, QS2 1, MPL and *Corynebacterium parvum*.

The immunogenic compositions, including vaccines, of the invention are prepared by techniques known to those skilled in the art, given the teachings contained herein. Generally, an immunogen mixed with the carrier to form a solution, suspension, or emulsion. One or more of the additives discussed above may be in the carrier or may be added subsequently. The vaccine preparations may be desiccated, for example, by freeze drying or spray drying for storage or formulations purposes. They may be subsequently reconstituted into liquid vaccines by the addition of an appropriate liquid carrier or administered in dry formulation known to those skilled in the art, particularly in capsules or tablet forms.

The immunogenic compositions, including vaccines, are administered to humans or other animals, preferably other mammals, such as ruminants, rodents and primates. They can be administered in one or more doses. The vaccines may be administered by known routes of administration. Many methods may be used to introduce the vaccine formulations described here. These methods include but are not limited to oral, intradermal, intramuscular, intraperitoneal, intravenous, subcutaneous, and intranasal routes. The preferred routes are intradermal, intramuscular or subcutaneous injection.

The invention also provides a method for inducing an immune response to Neisseria in an animal to generate a humoral and/or cellular immune response. The method comprises administering an immunologically effective amount of an immunogen of the invention to a host and, preferably, administering a vaccine of the invention to a host.

5.6. Nucleic Acids Encoding the NGSP Polypeptide and NGSP-derived Polypeptiedes The present invention also provides nucleic acids, DNA and RNA, encoding NGSP polypeptide and NGSP-derived polypeptides and pharmaceutical compositions comprising same. In a particular embodiment, the NGSP polypeptide comprises a deduced amino acid sequence as depicted in SEQ ID NOs: 4 or 6 and the nucleic acids comprise nucleotide sequences encoding said amino acid sequences. Particularly preferred fragments of NGSP have 5, 6, 7, or more deduced amino acid from the amino acid sequences depicted in SEQ ID NOs: 6, 7, 9 and 10 or sequences substantially homologous thereto and the invention encompasses nucleic acids comprising nucleotides encoding said amino acid sequences. In another particular embodiment, the NGSP polypeptide is encoded by the nucleotide sequence of SEQ ID NOs: 3 or 5, with particularly preferred fragments of nucleic acid depicted in SEQ ID NO: 8 or sequences substantially homologous thereto.

Nucleic acids of the present invention can be single or double stranded. The invention also provides nucleic acids hybridizable to or complementary to the foregoing sequences. In specific aspects, nucleic acids are provided which comprise a sequence complementary to at least 10, 15, 25, 50, 100, 200, or 250 contiguous nucleotides of a nucleic acid encoding NGSP polypeptide or an NGSP-derived polypeptide. In a specific embodiment, a nucleic acid which is hybridizable to a nucleic acid encoding NGSP polypeptide (e.g., having sequence SEQ ID NO.: 3 or 5), or to a nucleic acid encoding an NGSP-derived polypeptide, under conditions of low stringency is provided.

By way of example and not limitation, procedures using such conditions of low stringency are as follows (see also Shilo and Weinberg, 1981, Proc. Natl Acad. Sci. USA 78:6789–6792): Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5–20 X $10^6$ cpm $^{32}$P-labeled probe is used. Filters are incubated in hybridization mixture for 18–20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are-washed for a third time at 65–68° C. and re-exposed to film. Other conditions of low stringency which may be used are well known in the art (e.g., as employed for cross-species hybridizations).

In another specific embodiment, a nucleic acid which is hybridizable to a nucleic acid encoding NGSP polypeptide or an NGSP-derived polypeptide under conditions of high stringency is provided. By way of example and not limitation, procedures using such conditions of high stringency are as follows: Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0:02% BSA, and 500 µg/ml denatured salmon sperm DNA. Filters are hybridized for 48 h at 65° C. in prehybridization mixture containing 100 µg/ml denatured salmon sperm DNA and 5–20×$10^6$ cpm of $^{32}$P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency which may be used are well known in the art.

In another specific embodiment, a nucleic acid which is hybridizable to a nucleic acid encoding NGSP polypeptide or an NGSP-derived polypeptide under conditions of moderate stringency is provided.

Various other stringency conditions which promote nucleic acid hybridization can be used. For example, hybridization in 6×SSC at about 45° C., followed by washing in 2×SSC at 50° C. may be used. Alternatively, the salt concentration in the wash step can range from low stringency of about 5×SSC at 50° C., to moderate stringency of about 2×SSC at 50° C., to high stringency of about 0.2×SSC at 50° C. In addition, the temperature of the wash step can be increased from low stringency conditions at room temperature, to moderately stringent conditions at about 42° C., to high stringency conditions at about 65° C. Other conditions include, but are not limited to, hybridizing at 68° C. in 0.5M $NaHPO_4$ (pH7.2)/1 mM EDTA/7% SDS, or hybridization in 50% formamide/0.25M $NaHPO_4$ (pH 7.2)/0.25 M NaCl/1 mM EDTA/7% SDS; followed by washing in 40 mM $NaRPO_4$ (pH 7.2)/1 mM EDTA/5% SDS at 42° C. or in 40 mM $NaHPO_4$ (pH7.2) 1 mM EDTA/1% SDS at 50° C. Both temperature and salt may be varied, or alternatively, one or the other variable may remain constant while the other is changed.

Low, moderate and high stringency conditions are well known to those of skill in the art, and will vary predictably depending on the base composition of the particular nucleic acid sequence and on the specific organism from which the nucleic acid sequence is derived. For guidance regarding such conditions see, for example, Sambrook et al., 1989, Molecular Cloning, A Laboratory Manual, Second Edition, Cold Spring Harbor Press; N.Y., pp. 9.47–9.57; and Ausubel et al., 1989, Current Protocols in Molecular Biology, Green Publishing Associates and Wiley Interscience, N.Y.

Nucleic acids encoding NMAP-derived polypeptides, including but not limited to fragments or a portion thereof, (see Section 5.2), and NGSP antisense nucleic acids are additionally provided. As is readily apparent, as used herein, a "nucleic acid encoding a fragment or portion of a nucleic acid encoding NGSP polypeptide or an NGSP-derived polypeptide" shall be construed as referring to a nucleic acid encoding only the recited fragment or portion of the nucleic acid encoding NGSP polypeptide or an NGSP-derived polypeptide and not the other contiguous portions of the nucleic acid encoding NGSP polypeptide or an NGSP-derived polypeptide protein as a continuous sequence.

Also encompassed are nucleotide sequences substantially homologous to the above described nucleic acids. As used herein a "substantially homologous" sequence is at least 70%, preferably greater than 80%, more preferably greater than 90% identical to a reference sequence of identical size or when the alignment or comparison is conducted by a computer homology program or search algorithm known in the art.

By way of example and not limitation, useful computer homology programs include the following. Basic Local Alignment Search Tool (BLAST) (Altschul et al., 1990, *J. of Molec. Biol.*, 215:403410, "The BLAST Algorithm; Altschul et al., 1997, *Nuc. Acids Res.* 25:3389–3402) a heuristic search algorithm tailored to searching for sequence similarity which ascribes significance using the statistical methods of Karlin and Altschul (1990, *Proc. Nat'l Acad. Sci. USA*, 87:2264–68; 1993, *Proc. Nat'l Acad. Sci. USA* 90:5873–77). Five specific BLAST programs are provided and the BLASTN program compares a nucleotide query sequence against a nucleotide sequence database. Additional algorithms which can be useful are the Smith-Waterman and FASTA algorithms. See supra Section 5.1 for a more detailed description of useful algorithms and parameters for determining percent identity of nucleotide (and/or amino acid) sequences.

In one aspect, the nucleic acids of the invention may be synthesized using methods known in the art. Specifically, a portion of or the entire amino acid sequence of NGSP polypeptide or an NGSP-derived polypeptide may be determined using techniques well known to those of skill in the art, such as via the Edman degradation technique (see, e.g., Creighton, 1983, Proteins: Structures and Molecular Principles, W. H. Freeman & Co., N.Y., pp.34–49). The amino acid sequence obtained is used as a guide for the synthesis of DNA encoding NGSP polypeptide or NGSP-derived polypeptide using conventional chemical approaches or polymerase chain reaction (PCR) amplification of overlapping oligonucleotides.

In another aspect, the amino acid sequence may be used as a guide for synthesis of oligonucleotide mixtures which in turn can be used to screen for NGSP polypeptide coding sequences in Neisseria genomic libraries and PCR amplification products. Preferably the DNA used as the source of the NGSP polypeptide coding sequence, for both genomic libraries and PCR amplification, is prepared from cells of any Neisseria, including, but not limited to, *Neisseria ovis*, *Neisseria lacunata*, *Neisseria osloensis*, *Neisseria bovis*, *Neisseria meningitidis* (N.m.) particularly including types A–L and W, and *Neisseria gonorrhoeae* (N.g.). Preferred species are N.g. Strains from any of these organisms may be obtained worldwide from any biologicals depository, particularly strains of N.g. ATCC 9793, ATCC 9827, ATCC 9828, ATCC 9830, ATCC 10150, ATCC 10874, ATCC 11688, ATCC 11689, ATCC 19088, ATCC 19424, ATCC 21823, ATCC 21824, ATCC 21825, ATCC 23050, ATCC 23051, ATCC 27628, ATCC 27629, ATCC 27630, ATCC 27631, ATCC 27632, ATCC 27633, ATCC 31148, ATCC 31149, ATCC 31150, ATCC 31151, ATCC 31356, ATCC 31397, ATCC 31398, ATCC 31399, ATCC 31400, ATCC 31401, ATCC 31402, ATCC 31403, ATCC 31404, ATCC 31405, ATCC 31406, ATCC 31407, ATCC 31426, ATCC 31953, ATCC 33084, ATCC 35201, ATCC 35541, ATCC 35542, ATCC 43069, ATCC 43070, ATCC 43785, ATCC 49226, ATCC 49498, ATCC 49759, ATCC 49926, ATCC 49981, ATCC 51109, ATCC 51803, ATCC 51804, ATCC 53420, ATCC 53421, ATCC 53422, ATCC 53423, ATCC 53424, and ATCC 53425.

In the preparation of genomic libraries, DNA fragments are generated, some of which will encode parts or the whole of Neisseria NGSP polypeptide. The DNA may be cleaved at specific sites using various restriction enzymes. Alternatively, one may use DNase in the presence of manganese to fragment the DNA, or the DNA can be physically sheared, as for example, by sonication and the like. The DNA fragments can then be separated according to size by standard techniques, including but not limited to, agarose and polyacrylamide gel electrophoresis, column chromatography and sucrose gradient centrifugation. The DNA fragments can then be inserted into suitable vectors, including but not limited to plasmids, cosmids, bacteriophages lambda or $T_4$, and yeast artificial chromosome (YAC). (See, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U. K. Vol. I, II.) The genomic library may be screened by nucleic acid hybridization to labeled probe (Benton and Davis, 1977, Science 196:180; Grunstein and Hogness, 1975, Proc. Natl. Acad. Sci. U.S.A. 72:3961).

The genomic libraries may be screened with a labeled degenerate oligonucleotide probe corresponding to the amino acid sequence of any peptide fragment of the NGSP polypeptide using optimal approaches well known in the art. Any probe used preferably is 15 nucleotides or longer. Examples of particular probes are described below.

Clones in libraries with insert DNA encoding the NGSP polypeptide or fragments thereof will hybridize to one or more of the degenerate oligonucleotide probes. Hybridization of such oligonucleotide probes to genomic libraries are carried out using methods known in the art. Any of the hybridization procedures described in detail above in this Section can be used. For a specific illustrative example, hybridization with the two above-mentioned oligonucleotide probes may be carried out in 2×SSC, 1.0% SDS at 50° C. and washed using the same conditions.

In yet another aspect, clones of nucleotide sequences encoding a part or the entire NGSP polypeptide or NGSP-derived polypeptides may also be obtained by screening Neisseria expression libraries. For example, Neisseria DNA is isolated and random fragments are prepared and ligated into an expression vector (e.g., a bacteriophage, plasmid, phagemid or cosmid) such that the inserted sequence in the vector is capable of being expressed by the host cell into which the vector is then introduced. Various screening assays can then be used to select for the expressed NGSP polypeptide or NGSP-derived polypeptides. In one embodiment, the various anti-NGSP antibodies of the invention (see Section 5.5) can be used to identify the desired clones using methods known in the art. See, for example, Harlow and Lane, 1988, *Antibodies: A Laboratory Manual*, Cold Spring Harbor Laboratory Press, Cold Spring Harbor, N.Y., Appendix IV. Clones or plaques from the library are brought into contact with the antibodies to identify those clones that bind.

In an embodiment, colonies or plaques containing DNA that encodes NGSP polypeptide or NGSP-derived polypeptide could be detected using DYNA Beads according to Olsvick et al., 29th ICAAC, Houston, Tex. 1989, incorporated herein by reference. Anti-NGSP antibodies are crosslinked to tosylated DYNA Beads M280, and these antibody-containing beads then are used to adsorb to colonies or plaques expressing NGSP polypeptide or NGSP-derived polypeptide. Colonies or plaques expressing NGSP polypeptide or NGSP-derived polypeptide is identified as any of those that bind the beads.

Alternatively, the anti-NGSP antibodies can be nonspecifically immobilized to a suitable support, such as protein A or G resins, silica or Celite™ resin. This material is then used to adsorb to bacterial colonies expressing NGSP polypeptide or NGSP-derived polypeptide as described in the preceding paragraph.

In another aspect, PCR amplification may be used to produce substantially pure DNA encoding a part of or the whole of NGSP polypeptide from Neisseria genomic DNA. Oligonucleotide primers, degenerate or otherwise, corresponding to NGSP polypeptide sequences presently taught can be used as primers. In particular embodiments, a convergent set of oligonucleotides, degenerate or otherwise, specific for the NGSP coding sequences of SEQ ID NOs: 3 or 5 may be used to produce NGSP-encoding DNA.

As examples, an oligonucleotide encoding the N-terminal segment of the NGSP polypeptide may be used as the 5' forward primer, and together with a 3' reverse PCR oligonucleotide complementary to an internal, downstream protein coding sequence may be used to amplify an N-terminal-specific NGSP DNA fragment. Alternatively, an oligonucleotide encoding an internal NGSP coding sequence may be used as the 5' forward PCR primer together with a 3' reverse PCR oligonucleotide complementary to downstream, internal NGSP protein coding sequences may be used to PCR amplify an internal NGSP-specific DNA fragment. Alternatively the forward primer can be combined together with an oligonucleotide complementary to the C-terminal NGSP coding region to PCR amplify the NGSP ORF. These NGSP-specific PCR products can be cloned into appropriate expression vectors to direct the synthesis of all or part of the NGSP polypeptide. Alternatively, these NGSP-specific PCR products can be appropriately labelled and used as hybridization probes to identify all or part of the NGSP gene from genomic DNA libraries.

PCR can be carried out, e.g., by use of a Perkin-Elmer Cetus thermal cycler and Taq polymerase (Gene Amp™). One can choose to synthesize several different degenerate primers, for use in the PCR reactions. It is also possible to vary the stringency of hybridization conditions used in priming the PCR reactions, to allow for greater or lesser degrees of nucleotide sequence similarity between the degenerate primers and the corresponding sequences in Neisseria DNA. After successful amplification of a segment of the sequence encoding NGSP polypeptide, that segment may be molecularly cloned and sequenced, and utilized as a probe to isolate a complete genomic clone. This, in turn, permits the determination of the gene's complete nucleotide sequence, the analysis of its expression, and the production of its protein product for functional analysis, as described infra.

Once an NGSP polypeptide coding sequence has been isolated from one Neisseria species, strain or cultivar, it is possible to use the same approach to isolate NGSP polypeptide coding sequences from other Neisseria species, strains and cultivars. It will be recognized by those skilled in the art that the DNA or RNA sequence encoding NGSP polypeptide (or fragments thereof) of the invention can be used to obtain other DNA or RNA sequences that hybridize with it under conditions of moderate to high stringency, using general techniques known in the art. Hybridization with an NGSP sequence from one Neisseria strain or cultivar under high stringency conditions will identify the corresponding sequence from other strains and cultivars. High stringency conditions vary with probe length and base composition. The formulae for determining such conditions are well known in the art. See Sambrook et al., 1989, Molecular Cloning, A Laboratory Manual, Cold Spring Harbor Press, NY, Chapter 11. As used herein high stringency hybridization conditions as applied to probes of greater than 300 bases in length involve a final wash in 0.1×SSC/0.1% SDS at 68° C. for at least 1 hour (Ausubel, et al., Eds., 1989, Current Protocols in Molecular Biology, Vol. I, Greene Publishing Associates, Inc. and John Wiley & Sons, Inc., New York, at page 2.10.3). In particular embodiments, the high stringency wash in hybridization using a probe, for instance, having the sequence of SEQ ID NO:8 or 9 or its complement, is 2×SSC, 1% SDS at 50° C. for about 20 to about 30 minutes.

One skilled in the art would be able to identify complete clones of NGSP polypeptide coding sequence using approaches well known in the art. The extent of NGSP polypeptide coding sequence contained in an isolated clone may be ascertained by sequencing the cloned insert and comparing the deduced size of the polypeptide encoded by the open reading frames. (ORFs) with that of NGSP polypeptide and/or by comparing the deduced amino acid sequence with that of known amino acid sequence of purified NGSP polypeptide. Where a partial clone of NGSP polypeptide coding sequence has been isolated, complete clones may be isolated by using the insert of the partial clone as hybridization probe. Alternatively, a complete NGSP polypeptide coding sequence can be reconstructed from overlapping partial clones by splicing their inserts together.

Complete clones may be any that have ORFs with deduced amino acid sequence matching or substantially homologous to that of NGSP polypeptide or, where the complete amino acid sequence of the latter is not available, that of a peptide fragment of NGSP polypeptide and having a molecular weight corresponding to that of NGSP polypeptide. Further, complete clones may be identified by the ability of their inserts, when placed in an expression vector, to produce a polypeptide that binds antibodies specific to the amino-terminal of NGSP polypeptide and antibodies specific to the carboxyl-terminal of NGSP polypeptide.

Nucleic acid sequences encoding NGSP-derived polypeptides may be produced by methods well known in the art. In one aspect, sequences encoding NGSP-derived polypeptides can be derived from NGSP polypeptide coding sequences by recombinant DNA methods in view of the teachings disclosed herein. For example, the coding sequence of NGSP polypeptide may be altered creating amino acid substitutions that will not affect the immunogenicity of the NGSP polypeptide or which may improve its immunogenicity, such as conservative or semi-conservative substitutions as described above. Various methods may be used, including but not limited to oligonucleotide directed, site specific mutagenesis. These and other techniques known in the art may be used to create single or multiple mutations, such as replacements, insertions, deletions, and transpositions, as described in Botstein and Shortle, 1985, Science 229:1193–1210.

Further, DNA of NGSP polypeptide coding sequences may be truncated by restriction enzyme or exonuclease digestions. Heterologous coding sequence may be added to NGSP polypeptide coding sequence by ligation or PCR amplification. Moreover, DNA encoding the whole or a part of an NGSP-derived polypeptide may be synthesized chemically or using PCR amplification based on the known or deduced amino acid sequence of NGSP polypeptide and any desired alterations to that sequence.

The identified and isolated DNA containing NGSP polypeptide or NGSP-derived polypeptide coding sequence can be inserted into an appropriate cloning vector. A large number of vector-host systems known in the art may be used. Possible vectors include, but are not limited to, plasmids and modified viruses, but the vector system must be compatible with the host cell used. Such vectors include, but are not limited to, bacteriophages such as lambda derivatives, or plasmids such as pTrcHis, pBR322 or pUC plasmid derivatives. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved DNA may be modified by homopolymeric tailing. Recombinant molecules can be introduced into host cells via transformation, transfection, infection, electroporation, etc., so that many copies of the gene sequence are generated.

In an alternative method, the desired DNA containing NGSP polypeptide or NGSP-derived polypeptide coding sequence may be identified and isolated after insertion into a suitable cloning vector in a "shot gun" approach. Enrichment for the desired sequence, for example, by size fractionation, can be done before insertion into the cloning vector.

In specific embodiments, transformation of host cells with recombinant DNA molecules that contain NGSP polypeptide or NGSP-derived polypeptide coding sequence enables generation of multiple copies of such coding sequence. Thus, the coding sequence may be obtained in large quantities by growing transformants, isolating the recombinant DNA molecules from the transformants and, when necessary, retrieving the inserted coding sequence from the isolated recombinant DNA.

5.7. Recombinant Production of NGSP Polypeptide and NGSP-derived Polypeptides NGSP polypeptide and NGSP-derived polypeptides of the invention may be produced through genetic engineering techniques. In this case, they are produced by an appropriate host cell that has been transformed by DNA that codes for the polypeptide. The nucleotide sequence encoding NGSP polypeptide or NGSP-derived polypeptides of the invention can be inserted into an appropriate expression vector, i.e., a vector which contains the necessary elements for the transcription and translation of the inserted polypeptide-coding sequence. The nucleotide sequences encoding NGSP polypeptide or NGSP-derived polypeptides are inserted into the vectors in a manner that they will be expressed under appropriate conditions (e.g., in proper orientation and correct reading frame and with appropriate expression sequences, including an RNA polymerase binding sequence and a ribosomal binding sequence).

A variety of host-vector systems may be utilized to express the polypeptide-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA, or cosmid DNA. Preferably, the host cell is a bacterium, and most preferably the bacterium is E. coli, B. subtilis or Salmonella.

The expression elements of vectors vary in their strengths and specificities. Depending on the host-vector system utilized, any one of a number of suitable transcription and translation elements may be used. In a specific embodiment, a chimeric protein comprising NGSP polypeptide or NGSP-derived polypeptide sequence and a pre and/or pro sequence of the host cell is expressed. In other specific embodiments, a chimeric protein comprising NGSP polypeptide or NGSP-derived polypeptide sequence and an affinity purification peptide is expressed. In further specific embodiments, a chimeric protein comprising NGSP polypeptide or NGSP-derived polypeptide sequence and a useful immunogenic peptide or polypeptide is expressed. In preferred embodiments, NGSP-derived polypeptide expressed contains a sequence forming either an outer-surface epitope or the receptor-binding domain of native NGSP polypeptide.

Any method known in the art for inserting DNA fragments into a vector may be used to construct expression vectors containing a chimeric gene consisting of appropriate transcriptional/translational control signals and the polypeptide coding sequences. These methods may include in vitro recombinant DNA and synthetic techniques and in vivo recombinants (genetic recombination). Expression of a nucleic acid sequence encoding NGSP polypeptide or NGSP-derived polypeptide may be regulated by a second nucleic acid sequence so that the inserted sequence is expressed in a host transformed with the recombinant DNA molecule. For example, expression of the inserted sequence may be controlled by any promoter/enhancer element known in the art. Promoters which may be used to control expression of inserted sequences include, but are not limited to the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:3942) for expression in animal cells; the promoters of lactamase (Villa-Kamaroff et al., 1978, Proc. Natl. Acad. Sci. U.S.A. 75:3727–3731), tac (DeBoer et al., 1983, Proc. Natl. Acad. Sci. U.S.A. 80:21–25), $P_L$, or trc for expression in bacterial cells (see also "Useful proteins from recombinant bacteria" in Scientific American, 1980, 242:74–94); the nopaline synthetase promoter region or the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115–120) for expression implant cells; promoter elements from yeast or other fungi such as the Gal4 promoter, the ADC (alcohol dehydrogenase) promoter, PGK (phosphoglycerol kinase) promoter, alkaline phosphatase promoter.

Expression vectors containing NGSP polypeptide or NGSP-derived polypeptide coding sequences can be identified by three general approaches: (a) nucleic acid hybridization, (b) presence or absence of "marker" gene functions, and (c) expression of inserted sequences. In the first approach, the presence of a foreign gene inserted in an expression vector can be detected by nucleic acid hybridization using probes comprising sequences that are homologous to the inserted NGSP polypeptide or NGSP-derived polypeptide coding sequence. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if the NGSP polypeptide or NGSP-derived polypeptide coding sequence is inserted within the marker gene sequence of the vector, recombinants containing the insert can be identified by the absence of the marker gene function. In the third approach, recombinant expression vectors can be identified by assaying the foreign gene product expressed by the recombinant. Such assays can be based, for example, on the physical or functional properties of NGSP polypeptide or NGSP-derived polypeptide in in vitro assay systems, e.g., binding of a His tag to a column, binding to an NGSP ligand or receptor, binding with anti-NGSP antibodies of the invention, or serine protease activity.

Once a particular recombinant DNA molecule is identified and isolated, several methods known in the art may be used to propagate it. Once a suitable host system and growth conditions are established, recombinant expression vectors can be propagated and prepared in quantity. As explained above, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered NGSP polypeptide or NGSP-derived polypeptide may be controlled. Furthermore, different host cells have characteristic and specific mechanisms for the translational and post-translational processing and modification of proteins. Appropriate cell lines or host systems can be chosen to ensure the desired modification and processing of the foreign protein expressed.

5.8. Applications

The present invention has many utilities. For example, the NGSP polypeptide and NGSP-derived polypeptides may be used as ligands to detect antibodies elicited in response to Neisseria infections (e.g., as a diagnostic marker in diagnosing Neisseria infections). The NGSP polypeptide and NGSP-derived polypeptides may also be used as antigens or immunogens for inducing Neisseria-specific antibodies. Such antibodies are useful in immunoassays to detect Neisseria in biological specimens. The cytotoxic antibodies of the invention are useful in passive immunizations against Neisseria infections. The NGSP polypeptide, NGSP-derived polypeptides, and/or fragments thereof may further be used as active ingredients in vaccines to induce an immune response in an animal against Neisseria infections.

Not intending to be limited to any particular mechanism of action, the inventors provide the following remarks. The interaction of both normal and neoplastic mammalian cells with extracellular matrix components (ECM) such as fibronectin, vitronectin, and type I collagen has been shown to be mediated through a family of cell-surface receptors that specifically recognize an arginine-glycine-aspartic acid amino acid sequence within each protein (Ruoslahti E. and M. D. Pierschbacher. 1986. Arg-Gly-Asp: a versatile cell recognition signal. *Cell* 44:517–8). Numerous studies have shown that synthetic peptides containing the Arg-Gly-Asp sequence can inhibit these receptor-ligand interactions in vitro (Gehlsen K. R. Et al. 1988. Inhibition of in vitro tumor cell invasion by Arg-Gly-Asp-containing synthetic peptides. *J. Cell Biol.* 106:925–30). A highly active Arg-Gly-Asp sequence has been identified within the cell attachment region of fibronectin and the interaction between this sequence and specific platelet cell surface receptors has been demonstrated to induce activation. The conserved Arg-Gly-Asp and Arg-Gly-Asn motifs which reside near the C-terminus of the NGSP polypeptide of the present invention may also function as adherence domains specific for ECM proteins. If so, once the NGSP polypeptide of the present invention is bound to the host's cellular matrix the proteolytic activity of NGSP could function to remodel the epithelial/endothelial surface so as to promote attachment and or subsequent invasion. Thus using the NGSP polypeptides of the invention as a vaccine to produce antibody that could interrupt these processes would be beneficial.

The polypeptides, peptides, antibodies, nucleic acids and vectors comprising the nucleic acids, of the invention are useful as reagents for clinical or medical diagnosis of Neisseria infections and for scientific research on the properties of pathogenicity, virulence, and infectivity of Neisseria, as well as host defense mechanisms. For example, DNA and RNA of the invention can be used as probes to identify the presence of Neisseria in biological specimens by hybridization or PCR amplification. The DNA and RNA can also be used to identify other bacteria that might encode a polypeptide related to the Neisseria NGSP.

The polypeptides and peptides of the invention may be used to prepare polyclonal and monoclonal antibodies that can be used to further purify compositions containing the polypeptides of the invention by affinity chromatography. The polypeptides and peptides can also be used in standard immunoassays as diagnostics to screen for the presence of antibodies to Neisseria in a sample.

The nucleic acids, polypeptides and peptides of the invention are also useful in screening assays to detect compounds, including small molecules, or agents that are useful as diagnostic, therapeutic or prophylactic agents against Neisseria infection. In one illustrative mode of this embodiment, assays can be used to screen for a molecule or agent that binds to NGSP and hence which is useful as a diagnostic agent to detect Neisseria in a patient bodily fluid or tissue sample. In another illustrative mode of this embodiment, assays can be used to screen for a molecule or agent that targets NGSP polypeptide or the nucleic acid encoding NGSP polypeptide and hence which molecule or agent is useful as an antibacterial agent for therapy or prophylaxis against Neisseria infection. While not intending to be limited to any particular mode of action for the antibacterial agents identified according to the present invention, the inventors provide the following remarks. The novel NGSP polypeptide of the present invention has some limited sequence similarity to E. coli HtrA or DegP, including, but not limited to, conserved Arg-Gly-Asp and Arg-Gly-Asn motifs near the C-terminus of the NGSP polypeptide. The inventors envisage that molecules or agents that bind to, interact with, or inhibit the synthesis or enzymatic activity, such as but not limited to, serine protease activity, of the NGSP polypeptide of the invention are useful as anti-infective agents against Neisseria infection. Any assays known to those skilled in the art can be used according to this embodiment to screen for such agents. Non-limiting illustrative examples of assays include the following.

A number of systems have been described which can be adapted for the identification of agents interacting with NGSP polypeptide or NGSP derived polypeptides. One well known system is the yeast two-hybrid system (Fields and Song, 1989, Nature 340:245–246; White. 1996, Proc. Natl. Acad. Sci. USA 93:10001–10003; Warbick, 1997, Structure 5:13–17) which has been used to identify interacting proteins and to isolate the corresponding encoding genes. In this system, prototrophic selectable markers which allow positive growth selection are used as reporter genes to facilitate identification of protein-protein interactions. Applying the above general scheme, growing yeast cell colonies expressing DB-X/AD-Y-interacting proteins can be identified among the non-growing colonies (Gyris et al., 1993, Cell 75:791–803; Durfee et al., 1993, Genes Dev. 7:555–569; Vojtek et al., 1993, Cell 74:205–214). Related systems which may be employed include the yeast three-hybrid system (Licitra and Liu, 1996, Proc. Natl. Acad. Sci. USA 93:12817–12821; Tirode et al., 1997, J. Biol. Chem. 272:22995–22999) and the yeast reverse two-hybrid system (Vidal et al., 1996, Proc. Natl. Acad. Sci. USA 9:10321–10326; Vidal et al., 1996, Proc. Natl. Acad. Sci. USA 93:10315–10320).

Bacterial systems for identification of protein-protein interactions are also known in the art and may be adapted for use with the methods of the present invention. For example, in one embodiment, the E. coli CadC-based dimer detection system may be used for identifying proteins interacting with NGSP (see generally, PCT publication no. WO 99/23116 dated May 14, 1999, which is incorporated herein in its entirety). In another embodiment, a bacterial protein interaction system based on the AraC protein, which regulates the L-arabinose operon in E. coli, may be used (Bustos and Schleif, 1993, Proc. Natl. Acad. Sci. USA 9:5638–5642; Soisson et al., 1997, Science 27:421425; Eustance et al., 1994, J. Mol. Biol. 242:330–338). Other assay systems which may be used include bacterial systems based on the lambda repressor system (Zeng et al., 1997, Protein Sci. 6:2218–2226), the lac-operon (Gates et al., 1996, J. Mol. Biol. 255:373–386), an interaction signal detection based on lambda and lambda proteins (Hollis et al., 1988. Proc. Natl. Acad. Sci. USA 85:5834–5838), systems based on E. coli RNAP (Dove et al., 1998, Genes Dev. 12:745–754; Dove et al., 1997, Nature 386:627–630), and systems based on the cAMP synthetase (Karimova et al., 1998, Proc. Natl. Acad. Sci. USA 95:5752–5756).

Alternatively, assays screening for interaction of molecules with NGSP can be devised using a detectible marker. Proteins or other molecules may be labeled with a detectable marker using methods for protein labeling known in the art. A "detectable marker" refers to a moiety, such as a radioactive isotope or group containing same, or nonisotopic labels, such as enzymes, biotin, avidin, streptavidin, digoxygenin, luminescent agents, dyes, haptens, and the like. Luminescent agents, depending upon the source of exciting energy, can be classified as radioluminescent, chemiluminescent, bioluminescent, and photoluminescent (including fluorescent and phosphorescent). An affinity capture assay may be used.

In another embodiment, any molecule including macromolecules and small molecules, can be assayed for interaction with NGSP polypeptide or an NGSP-derived polypeptide; interaction with NGSP or an NGSP-derived polypeptide indicates the molecule is useful as a diagnostic, therapeutic or prophylactic against Neisseria infection. In one embodiment, the method is as follows. A method for assaying for an agent that interacts with NGSP polypeptide comprises: (a) contacting a cell expressing NGSP polypeptide with an agent labeled with a detectable marker for a time sufficient to allow the agent to interact with the polypeptide; (b) washing the cells; and (c) detecting any marker associated with the cells, in which any cell associated marker indicates that the agent interacts with the NGSP polypeptide and wherein any agent that interacts with NGSP indicates that the agent is useful as a diagnostic, prophylactic or therapeutic agent against Neisseria infection.

DNA or polypeptides of the invention may be used to assess the binding of small molecule substrates and ligands in, for example, cells, cell free preparations, chemical libraries, and natural product extracts and mixtures. These substrates and ligands may be natural substrates and ligands or may be structural or functional mimetics thereof.

The invention also provides a method of screening compounds to identify those which enhance (i.e., agonists) or block (i.e., antagonists) of the action of NGSP polypeptides, particularly those compounds that are bacteriostatic or bactericidal. The method of screening may involve high-throughput assay techniques. For example, to screen for agonists or antagonists, a synthetic reaction mix, a cellular compartment, such as a membrane, cell envelope or cell wall, or a preparation of any mixture thereof, comprising NGSP polypeptide and a labeled substrate or ligand of such polypeptide is incubated in the absence or the presence of a candidate molecule that may be a NGSP agonist or antagonist. The ability of the candidate molecule to agonize or antagonize the NGSP polypeptide is reflected in decreased binding or the labeled ligand or decreased production of product from such substrate. Molecules that bind gratuitously, i.e., without inducing the effects of NGSP polypeptide are most likely to be good antagonists. Molecules that bind well and increase the rate of product production from substrate are agonists. Detection of the rate or level of production of product from substrate may be enhanced by using a reporter system. Reporter systems that may be useful in this regard include but are not limited to colorimetric labeled substrate converted into product, a reporter gene that is responsive to change in a NGSP polypeptide activity, and binding assays known in the art. Potential antagonists or agonists include small molecules, peptides, and antibodies that bind to a NGSP peptide or polypeptide or the invention, or such a closely related protein or antibody that binds the same sites on a binding molecule.

It is to be understood that the application of the teachings of the present invention to a specific problem or environment will be within the capabilities of one having ordinary skill in the art in light of the teachings contained herein.

The above disclosure generally describes the present invention. A more specific description of certain embodiments is provided below in the following examples. The examples are described solely for the purpose of illustration and are not intended to limit the scope of the invention. Changes in form and substitution of equivalents are contemplated as circumstances suggest or render expedient. Although specific terms have been employed herein, such terms are intended in a descriptive sense and not for purposes of limitation.

Methods of molecular genetics, protein biochemistry and immunology used but not explicitly described in the disclosure and examples are amply reported in the scientific literature and are well within the ability of those skilled in the art.

6. EXAMPLE

Isolation and Characterization of the NGSP Polypeptide and Sequence Encoding Same

6.1. Extraction of Envelope Proteins

Neisseria are grown at 37° C. at 200 rpm in 1 liter of Mueller Hinton broth, chocolate agar plates or Columbia blood agar plates. Extraction with hypotonic solutions is carried out as follows. Cells are harvested into lithium chloride (LiCl), sodium acetate (NaOAc) solution (0.1M LiCl, 0.2 M NaOAc, pH 5.8) and shaken with glass beads for 3 h in a 45° C. water bath. The beads and cellular debris are removed by centrifugation and for crude extracts, the supernatant removed and stored at −20° C. For purified extracts, the supernatant is furthers centrifuged at 100,000×g and the resulting pellet resuspended and either stored or used for further purification as described herein.

Extraction using detergents is carried out as follows. Cells are harvested into a Tris-hydrochloride buffer solution and pelleted by centrifugation. The pelleted cells are resuspended and sonicated to disrupt the cells. Unbroken cells are removed by low speed centrifugation and the total cell envelope fraction is treated with either (1.25% final w/v) n-octyl-D- glucopyranoside (i.e., octyl glucoside; OG) in phosphate buffered saline (PBS) or (0.5% w/v) of sodium N-lauroyl sarcosine (Sarkosyl) for 30 minutes at room temperature. The unsolublized fraction is pelleted and the supernatant is used as the detergent extract for resolution using SDS-PAGE or for further purification as described herein.

6.2. Amino Terminal Sequencing of NGSP Polypeptide

NGSP polypeptide from extracts of Neisseria is detected (e.g., by silver staining or anti-NGSP antibodies) in denaturing gels. For N-terminal sequencing, an extract is mixed with PAGE sample buffer containing SDS, and is incubated for 3 minutes in boiling water bath. The proteins are then resolved on a PAGE with SDS and transferred to a PVDF membrane by electroblotting. The region of the membrane containing the NGSP band is then cut out and aminoterminal sequencing is performed by generally accepted methods known to those skilled in the art.

6.3. Anti-NGSP Antiserum

Antisera to NGSP are prepared by injecting the NGSP polypeptide into an animal, such as a rabbit, mouse or guinea pig, with or without an adjuvant. For instance, NGSP is injected with Freund's complete adjuvant followed by injections of NGSP with Freund's incomplete adjuvant. Normally, an isolated, a semi-purified or purified form of the protein is injected. For instance, the NGSP polypeptide is resolved from other proteins using a denaturing sodium dodecylsulfate polyacrylamide gel according to standard techniques well known to those skilled in the art, as previously described (Laemmli, 1970, Nature 227:680–685), and cutting the NGSP-containing band out of the gel. The excised band containing NGSP is macerated and injected into an animal to generate antiserum to the NGSP polypeptide. The antisera is examined using well known and generally accepted methods of ELISA to determine titres, by western blots to determine binding to proteins, for immunofluorescent staining and for complement-mediated cytotoxic activity against Neisseria as described below.

6.4. Western Blots

*Neisseria gonorrhoeae* (clinical isolate) is grown on gonococcal agar (GC agar base, Difco; supplemented with 1% IsoVitale X, BBL) or chocolate agar plates for 24–48 hours at 37° C. in 5% $CO_2$. Cells are removed by scraping the colonies from the agar surface using a polystyrene inoculating loop. Cells are then solubilized by suspending 30 $\mu$g of cells in 150 $\mu$l of PAGE sample buffer (360 mM Tris buffer [pH 8.8], containing 2-mercaptoethanol, 4% sodium dodecylsulfate and 20% glycerol), and incubating the suspension at 100° C. for 5 minutes. The solubilized cells are resolved on 12% polyacrylamide gels as per Laemmli and the separated proteins were electrophoretically transferred to PVDF membranes at 100 V for 1.5 hours as previously described (Thebaine et al. 1979, Proc. Natl. Acad. Sci. USA 76:4350–4354). The PVDF membranes are then pretreated with 25 ml of Dulbecco's phosphate buffered saline containing 0.5% sodium casein, 0.5% bovine serum albumin and 1% goat serum. All subsequent incubations are carried out using this pretreatment buffer.

PVDF membranes are incubated with 25 ml of a 1:500 dilution of preimmune rabbit serum or serum from a rabbit immunized with NGSP or Hin47 polypeptide (as described above) for I hour at room temperature or monoclonal antibodies to NGSP or to Hin47 (described above). PVDF membranes are then washed twice with wash buffer (20 mM Tris buffer [pH 7.5.] containing 150 mM sodium chloride and 0.05% TWEEN-20™ (polyoxyethenlenesorbitan monolaureate"). PVDF membranes are incubated with 25 ml of a 1:5000 dilution of peroxidase-labeled goat anti-rabbit (or anti-mouse for monoclonals) IgG (Jackson ImmunoResearch Laboratories, West Grove, Pa.) for 30 minutes at room temperature. PVDF membranes are then washed 4 times with wash buffer, and are developed with 3,3'diaminobenzidine tetrahydrochloride and urea peroxide as supplied by Sigma Chemical Co. (St. Louis, Mo. catalog number D-4418) for 4 minutes each.

6.5. Anti-NGSP Immunofluorescence Staining of Cell Surface

Neisseria are grown overnight at 37° C. in a shaking water bath in Mueller Hinton broth or on gonoccal agar and harvested by scraping. The cells are pelleted by centrifugation and then resuspended in an equal volume of Dulbecco's modification of phosphate buffered saline without calcium or magnesium (PBS/MC). 20 µl of the cell suspension is applied to each of 5 clean microscope slides. After setting for 10 seconds, the excess fluid is removed with a micropipettor, and the slides are allowed to air dry for 1 hour. The slides are then heat fixed over an open flame until the glass is warm to the touch. The slides are initially treated with 40 µl of 1:40 dilution of anti-NGSP antiserum or preimmune serum from the same animal diluted in PBS/MC, or PBS/MC for 10 minutes, then washed 5 times with PBS/MC. The slides are treated with 40 µl of 5 µg/ml PBS/MC of fluorescein isothiocyanate-labeled goat antibody to rabbit IgG (Kirkegaard and Perry Laboratories, Inc, Gaithersburg, Md.). The slides are incubated in the dark for 10 minutes and are washed 5 times in PBS/MC. Each slide is stored covered with PBS/MC under a cover slide and is viewed with a fluorescence microscope fitted with a 489 nm filter. For each sample five fields-of-view are visually examined to evaluate the extent of straining.

6.6. Cellular Envelope Location of NGSP

Rabbit anti-NGSP antiserum is used in indirect immunofluorescence staining to determine if NGSP polypeptide is exposed on the outer surface of Neisseria cells. This would indicate that in intact Neisseria cells NGSP polypeptide is reactive with anti-NGSP antibodies.

6.7. Properties of NGSP Polypeptide

NGSP polypeptide exists as a protein of approximately 40–55 kD in its native state as can be determined using detergent or hypotonic extracts of Neisseria, incubating the extracts with sodium dodecyl sulfate at 100° C., and resolving the proteins on a denaturing polyacrylamide gel.

Western blot analysis of protein extracts of a number of Neisseria strains can be used to show that the anti-NGSP antibodies bind to a polypeptide of about 40 kD to about 55 kD in many Neisseria strains. Anti-NGSP antibodies may be used to specifically identify Neisseria. NGSP polypeptide may be used to generate antibodies that have diagnostic application for identification of Neisseria. Antibodies to NGSP polypeptide of one species or strain may be used to identify and isolate the corresponding NGSP polypeptide of other Neisseria species or strains.

7. EXAMPLE

Efficacy of NGSP Vaccine

Cytotoxic Activity of Anti-NGSP Antiserum

Complement-mediated cytotoxic activity of anti-NGSP antibodies is examined to determine the vaccine potential of NGSP polypeptide. Antiserum to NGSP polypeptide is prepared as described in Section 6.3. supra. The activities of the pre-immune serum and the anti-NGSP antiserum in mediating complement killing of Neisseria are examined using a "Serum Bactericidal Test," for instance, as described by Zollinger et al. (Immune Responses to *Neisseria meningitis*, in *Manual of Clinical Laboratory Immunology*, 3rd ed., pg 347–349). The results are used to show that anti-NGSP antiserum mediates complement-killing of Neisseria.

8. EXAMPLE

Isolation of the NGSP Nucleic Acid Sequencer

8.1. Identification of a NGSP Open Reading Frame

The *E. coli* DegP (HtrA) amino acid sequence available from GeneBank was employed as a BLAST (TBLASTN) subject query to search the genomic sequence databases for *N.gonorrhoeae* (Univ. Oklahoma, USA) strain 1090 to identify linear amino acid sequences that might share some similarity to the DegP protein. No predicted amino acid sequences from this Neisseria database showed more than ~30–35% similarity to the *E. coli* DegP protein sequence. Candidate *N.gonorrhoeae* NGSP amino acid sequences were localized within specific genomic DNA sequence "contigs", and putative open reading frames encoding these NGSP sequences were derived. Putative ORFs capable of encoding proteins of ~40–55 kD, the average size of most DegP-like serine proteases, were then selected and further analyzed for the presence and appropriate relative spacing of semi-conserved catalytic residues (H, D, S) thought to be required for serine protease activity. A single putative open reading frame from the *N.gonorrhoeae* database was identified which met these criteria.

8.2. Isolation of *N. gonorrhoeae* Chromosomal DNA

*N.gonorrhoeae* strain GC340 was obtained from the Centers for Disease Control and Prevention (CDC). GC340 was streaked on gonococcal agar base (GC agar™, Difco) containing 1.0% IsoVitale™ X (BBL) and grown at 35–37° C. in 5% $CO_2$ for ~24–28 hours. To prepare confluent "lawns" of cells for DNA isolation, three or four single colonies were picked from the "overnight" seed plate and used to inoculate fresh GC plates which were again grown overnight at 35–37° C. in 5% $CO_2$. Cells were collected from the surface of the agar plates by gentle rinsing using trypticase soy broth (TSB) containing 10% glycerol and then stored at –20° C. When needed, cells were thawed at room temperature and bacteria collected by centrifugation in a Sorval SS34 rotor at ~2000 Xg for 15 minutes at room temperature. The supernatant was removed and the cell pellet suspended in 5.0ml of sterile water. An equal volume of lysis buffer (200 mM NaCl, 20 mM EDTA, 40 mM Tris-HCl pH8.0, 0.5% (w/v) SDS, 0.5% (v/v) 2-mercaptoethanol, and 250 ug/ml of proteinase K) was added and the cells suspended by gentle agitation and trituration. The cell suspension was then incubated ~12 hours at 50° C. to lyse the bacteria and liberate chromosomal DNA. Proteinaceous material was precipitated by the addition of 5.0 ml of saturated NaCl (~6.0M, in sterile water) and centrifugation at ~5,500×g in a Sorval SS34 rotor at room temperature. Chromosomal DNA was precipitated from the cleared supernatant by the addition of two volumes of 100% ethanol. Aggregated DNA was collected and washed using gentle agitation in a small volume of a 70% ethanol solution. Purified chromosomal DNA was suspended in sterile water and allowed to dissolve/disburse overnight at 4° C. by gentle rocking. The concentration of dissolved DNA was determined spectrophotometrically at 260 nm using an extinction coefficient of 1.0 O.D. unit ~50 ug/ml.

83. PCR Cloning of the NGSP ORF

To produce high levels of recombinant *N.gonorrhoeae* NGSP protein for immunogenicity and protective efficacy studies the NGSP ORF was PCR cloned into an *E.coli* high expression vector under the control of the trc promoter. Oligonucleotide PCR primers complementary to the DNA sequences encoding the first 10 amino acid residues of the N-terminus (VFKKYQYFAL) (SEQ ID NO: 9) and the last 11 C-terminal amino acid residues (EILAVRASPRQ) (SEQ ID NO: 10) of the *N.gonorrhoeae* NGSP ORF present in the Oklahoma genomic database were synthesized. In addition to the NGSP specific sequences, these PCR primers were designed to contain flanking EcoRI and SalI restriction sites, respectively, in an effort to expedite directional cloning of the ORF into the expression vector pTLZ2. These oligonucleotides were used to amplify NGSP-specific PCR products from the clinically relevant *N.gonorrhoeae* strain GC340.

The amplification primers used for these PCR reactions were designated NgH47-Fn/t-RI (46 mer, forward primer) and NgH47-RCh/t-Sal (69 mer, reverse primer). In addition to the NGSP coding sequences, the forward primer was designed to contain a unique EcoRI restriction site located upstream of the NGSP ORFs Met initiation residue. The reverse primer was designed to contain six contiguous His codons (CAT or CAC) immediately downstream and in the same translational reading frame as the 3' NGSP coding sequence. A unique SalI restriction site was engineered into the reverse primer downstream and adjacent to a translatoin stop codon (TAA) that follows the last His codon to facilitate directional cloning into pTLZ2. Thus recombinant NGSP protein expressed from the insert amplified using the NgH47-Fn/t-RI and NgH47-RCh/t-Sal primers will carry a (His)$_6$ affinity purification tag at the C-terminus.

cloned genes, the procaryotic rrnB transcriptional stop sequence, and the highly efficient and regulated tac promoter.

Aliquots from the ligation reaction were then used to electrotransform a suitable *E.coli* host (e.g. JM109). Transformed cells were plated on 2X-YT agar containing 100 ug/ml ampicillin and grown at 37° C. for ~12–16 hours. Mini-prep DNA from ampicillin-resistant transformants picked at random were prepared using commercially available reagents (QiaGen Mini Prep Kit) and examined for the presence of recombinant plasmids larger than the ~4.8 Kbp vector plasmid pTLZ2 (i.e. insert-carrying plasmids). Putative NGSP-insert carrying recombinant plasmids were then digested to completion with EcoRI and SalI and examined for the presence of the ~1.4 Kbp NGSP-specific fragment by standard agarose gel electrophoresis (0.8% agarose, TAE buffer). All ~6.2 Kbp plasmids tested were found to contain the NGSP insert. Plasmid pTLZ-NgHtrA #2 was one recombinant derivative isolated by these procedures. A map of pTLZ-Ng HtrA#2 NGSP is presented in FIG. 1.

8.4. Expression of Recombinant NGSP Protein

The ability of pTLZ-NgHtrA #2 to express the *N.gonorrhoeae* recombinant NGSP protein was assessed by SDS-PAGE. A 5.0 ml overnight culture of JM109 (pTLZ-NgHtrA #2) was prepared in LB broth containing ampicillin (100 ug/ml) and inoculated with cells from a "patch" plate made directly from the original pTLZ-NgHtrA #2 transformant colony and grown overnight at 37° C. with shaking (~250 rpm). An aliquot of the overnight seed culture (~1.0 ml) was NgH47-Fn/t-RI (46 mer)                                                  (SEQ ID No. 1)
5'-AGG CAG AGG GAA TTC ATG TTC AAA AAA TAC CAA TAC TTC
GCT TTG G-3'

NgH47-Rch/t-Sal (69 mer)                                                (SEQ ID No. 2)
5'-AGG CAG AGG GTC GAC TAA ATG GTG ATG GTG ATG GTG TTG ACG GGG
ACT TGC CCT GAC GGC TAG GAT TTC-3'

Standard PCR amplification reactions (2 mM Mg$^{2+}$, 200 umol dNTPs, 0.75 units AmpliTaq, 50 ul final volume) were programmed using ~0.1 ug of *N.gonorrhoeae* GC340 chromosomal DNA. Amplification of the NGSP target sequence was achieved using a standard 32-cycle, three-step thermal profile, i.e. 95° C., 30 sec; 60° C., 45 sec, 72° C., 1 min. Amplification was carried out in 0.2 ml polypropylene thin-walled PCR tubes (Perkin-Elmer) in a Perkin-Elmer model 2400 thermal cycler. PCR amplification reactions produced the expected NGSP-specific ~1.4 Kbp amplimer.

The ~1.4 Kbp NGSP amplimer was purified from unincorporated primers using hydroxyapatite spin columns (QiaGen) and digested to completion with an excess of EcoRI and SalI (BRL, ~10 units per 1 ug DNA) according to the manufacturers recommendations. The purified and digested NGSP ORF was then purified via QiaGen columns as described above and cloned into plasmid pTLZ2 that had been previously digested to completion with both EcoRI and SalI and treated with calf intestinal alkaline phosphatase (BRL, ~0.05 units/pmole of 5' ends) to prevent vector religation (~5:1, insert:vector ratio).

Digestion of the ~7.9 Kbp pTLZ2 vector with EcoRI and SalI produces two restriction fragments; one a ~3.1 Kbp fragment encoding the *E.coli* β-galactosidase gene and the other a ~4.8 Kbp plasmid replicon containing the pBR322 origin of replication, an ampicillin resistance gene, the *E.coli* lacI$^q$ repressor for controlled expression of exogenous inoculated into a 125 ml erlenmeyer flask containing ~25 of LB/Ap broth and grown at 37° C. with shaking (~250 rpm) until the culture turbidity reached O.D.600 of ~0.5, i.e. mid-log phase (usually about 1.5–2.0 hours). At this time approximately half of the culture (~12.5 ml) was transferred to a second 125 ml flask and expression of recombinant NGSP protein induced by the addition of IPTG (1.0 M stock prepared in sterile water, Sigma) to a final concentration of 1.0 mM. Incubation of both the IPTG-induced and non-induced cultures continued for an additional ~4 hours at 37° C. with shaking.

Samples (~1.0 ml) of both induced and non-induced cultures were removed after the induction period and the cells collected by centrifugation in a microcentrifuge at room temperature for ~3–5 minutes. Individual cell pellets were suspended in ~50 ml of sterile water, then mixed with an equal volume of 2×Laemmli SDS-PAGE sample buffer containing 2-mercaptoethanol, and placed in boiling water bath for ~3–5 min to denature and reduce the recombinant protein. Equal volumes (~15 μl) of both the crude IPTG-induced and the non-induced cell lysates were loaded onto duplicate 4–20% Tris/glycine polyacrylamide gradient gels (1 mm thick Mini-gels, Novex).

The induced and non-induced lysate samples were electrophoresed together with prestained molecular weight markers (SeeBlue, Novex) under conventional electrophoresis conditions (~30 mA, constant current) using a standard SDS/Tris/glycine running buffer (BioRad). Following electrophoresis, one gel was stained with commassie brilliant blue R250 (BioRad) and then destained using an acetic acid:methanol:water destaining solution to visualize novel ~50 kDa NGSP arabinose-inducible protein.

The second gel was electroblotted onto a PVDF membrane (0.45 micron pore size, Novex) for ~2 hr at 4° C. using a BioRad Mini-Protean II blotting apparatus and Towbin's methanol (20%) transfer buffer. Blocking of the membrane and antibody incubations were performed using a Tris (50 mM, pH7.3):CaCl$_2$ (1 mM): TWEEN-20™ (polyoxyethenlenesorbitan monolaureate"). (0.2%) buffer containing 0.5% casein. A monoclonal anti-(His)$_5$ antibody conjugated to HRP (QiaGen) was used at a 1/5,000 dilution to confirm the expression and identify of ~50 kDa inducible rNGSP protein. Visualization of the antibody reactive pattern was achieved on Hyperfilm using the Amersham ECL chemiluminescence system. The results from the Western blot experiment are shown in FIG. 2.

8.5. Purification of Recombinant Protein

Recombinant NGSP protein is purified to homogeneity using standard preparative column chromatographic procedures. Briefly, an *E. coli* strain harboring the expression plasmid pTLZ-NgHtrA #2 is grown in Luria broth in a 51 fermenter (New Brunswick) at 37° C. with moderate aeration until mid-log phase (~0.5 O.D.$_{600}$) and induced with IPTG (1 mm final) for 4–5 hours. Cell paste is collected, washed in PBS and stored at –20° C. Aliquots of frozen cell paste (~9–10 g wet weight) are suspended in ~120 ml of D-PBS by mechanical agitation and lysed by passage through a French pressure cell (2×, 14,000psi, 4° C.). The exact sample preparation methodology to be used for NGSP purification varies somewhat depending on whether the NGSP protein is expressed as a soluble component or as insoluble inclusion bodies.

A general process for the purification of NGSP protein as a soluble protein is given below. Insoluble material is removed after French press disruption by high speed centrifugation (~10,000×g, 4° C., 30 min). The soluble fraction containing NGSP is suspended in ~20 ml of ice cold 50 mM Tris-HCl buffer (pH8.0) and loaded onto a DEAE-SEPHACEL™ (Diethylarninoethyl cellulose) (Pharmacia) ionic exchange column (~5×60 cm). To minimize autoproteolysis of the NGSP protein, chromatography is conducted at 4° C. Unbound material is washed from the column using loading buffer (50 mM Tris-Hcl, pH8.0) prior to elution of bound NGSP protein. Elution of NGSP from the SEPHACEL™ (cellulose) matrix is achieved using a NaCl gradient (0.05×0.5M NaCl, in 50 mM Tris-Hcl, pH8.0). Fractions released by the salt gradient are collected and examined by standard SDS-gel electrophoresis methodologies for the presence of a ~40–55 kd protein. Fractions are also assayed for protease activity using a standard azocasein colorimetric assay. Fractions containing NGSP are pooled and extensively dialyzed against 10 mM sodium phosphate buffer (SPB, pH8.0) at 4° C.

The partially purified NGSP is then applied to a hydroxylapatite column, previously equilibrated in SPB. Bound proteins are eluted using a 0.1–0.5M NaCl gradient in SPB. Fractions are collected periodically during elution and examined for the presence of NGSP by SDS-gel electrophoresis and protease activity as above. Eluted material is dialyzed against 50 mM Tris-HCl to remove residual salt and concentrated using a Centricon-30 concentrator (Amicon, 30,000 MWCO).

8.6. Generation of a Radiolabelled Screening Probe

The sequence information shown above is used to design a pair of nondegenerate convergent (i.e., one forward and one reverse primer) oligonucleotide primers. PCR amplification of DNA fragments is performed under the same conditions as described above with the exception that the annealing temperature is raised to 50° C. The DNA fragment is isolated from an agarose gel as before and readiolabelled using (32 P)-gamma-ATP and T4 polynucleotide kinase according to standard methods. Unincorporated radiolabel is separated from the probe on a G25 SEPHAROSE™ (Agarose) spin column. Before use, the probe is denatured for 2 min. at 95° C. and subsequently chilled on ice (4° C.).

8.7. Hybridization of Plaque-lift Filters and Southern Blots With Radiolabelled Probe Phage plaques from library platings are immobilized on nylon filters using standard transfer protocols well known to those skilled in the art. Digested bacterial genomic DNA, phage or plasmid DNA is electrophoresed on 0.8% TAE-agarose gels and transferred onto nylon filters using a pressure blotter (Stratagene) according to the manufacturer's recommendations. Hybridizations with selected probes are performed at 37° C. Hybridizations with other probes are generally carried out at 60° C. Washes of increasing stringency are done at the respective hybridization temperatures until nonspecific background is minimized.

8.8. Construction of a *Neisseria Gonorrhoeae* Genomic DNA Library

A genomic library is constructed in the λZAPII replacement vector obtained from Stratgene. The vector arms are digested with EcoRI. Digests of *Neisseria gonorrhoeae* DNA by EcoRI are performed to yield fragment sizes between 1 kb and 5 kb. Ligations of vector arms and insert DNA are carried out according to standard protocols. Ligation reactions are packaged in vitro using the Stratagene GigaPack Gold III extract. The packaged phage are plated on *E. coli* Xl Blue MRA (P2) (Stratagene). An initial library titer is determined and expressed as number of pfu.

The library is screened using 4×10$^4$ pfu that are plated at a density of 8×10$^3$ pfu/130 mm plate. Several putative positive phage plaques are identified by screening the library with a radiolabelled NGSP-specific DNA hybridization probe or a NGSP-monospecific antibody and the strongest hybridizing phage are eluted from cored agarose plugs, titered and replated for secondary screening. The selected phages are replated at low density (approximately 100 pfu/plate) and plaques are analyzed by PCR using primer pairs. Inserts carrying plasmids (phagemids) are rescued from the selected phage by co-infecting *E. coli* cells with an appropriate helper virus.

8.9. Determination of Insert Size and Mapping of DNA Fragments

In order to estimate the size of inserts, phagemid DNA is digested with NotI and the digests are analyzed on a 0.5% TAE-agarose gel side by side with suitable DNA markers. In order to map restriction fragments that would hybridize to the probe, DNA from phagemid isolates is digested with a number of common restriction enzymes either alone or in combination with NotI. The rationale of this approach is to discriminate between fragments that span the insert/phagemid vector junction and those that map on the NotI insert. The series of single and double digests are run side-by-side for each phage isolate and analyzed by Southern analysis with radiolabelled probe.

9. EXAMPLE

Sequencing of the NGSP Nucleic Acid

Sequencing of the NGSP encoding nucleic acid from pTLZ-NgHtrA#2 is performed using the plasmid pTLZ-NgHtrA#2 as a template. All sequencing reactions are performed using the Dye Terminator Cycle Sequencing Kit from Perkin-Elmer according to the manufacturer's specifications. The sequencing reactions are read using an ABI Prism 310 Genetic Analyzer. The sequences are aligned using the AutoAssembler software (Perkin-Elmer) provided with the ABI Prism 310 sequencer. This plasmid was inserted into E. coli JM109 (Invitrogen) and deposited with American Type Culture Collection (ATCC) as E. coli JM 109 (pTLZ-NgHtrA#2).

The nucleotide sequence of the NGSP gene is shown in SEQ ID NO:3. A deduced amino acid sequence of the open reading frame of NGSP is shown in SEQ ID NO:4.

10. EXAMPLE

Geneticanalysis

10.1. Knock-out Mutants

A genomic knock-out mutation of the NGSP gene is constructed using standard methodologies. For example, the NGSP gene from strain GC340 which has been cloned into a suitable plasmid vector, e.g., plasmid pTLZ-N&HtrA#2, is digested with a restriction enzyme (e.g., AscI) that cuts the NGSP gene only once. The digested NGSP plasmid is then ligated to a DNA fragment encoding a suitable resistance marker, e.g., the kanamycin resistance ($KAN^R$) cassette from plasmid pUC4-K. The ligation mixture is then used to transform E. coli cells to $KAN^R$. Once the presence of the $KAN^R$-insert is confirmed by restriction analysis, these cloned NGSP $KAN^R$-derivatives are used to transform competent N.gonorrheoeae. Although N.gonorrhoeae are naturally competent, standard procedures are used to enhance transformation efficiency. Transformants are analyzed by Southern blotting and/or PCR to identify knockout mutants that have recombined the NGSP-$KAN^R$ cassette into the chromosome.

10.2. PCR Analysts

DNA from $KAN^R$ Neisseria gonorrhoeae colonies is analyzed by PCR using primers that hybridize to flanking sequences upstream and downstream of the NGSP gene. A PCR product equal in size to the native gene is only to be expected if the incoming targeting cassette has not been integrated into the genome by homologous recombination. Amplification products longer than the native gene are obtained only when the KanR cassette has been successfully integrated.

10.3. Southern Analysis of NGSP

Genomic DNA from wild-type Neisseria gonorrhoeae and from PCR positive deletion mutants is digested with EcoRI. The digests are separated on a 0.8% TAE-agarose gel and transferred to nylon membranes using standard protocols. The blots are hybridized with $^{32}P$ labeled probes prepared from either the NGSP region or from the Kanamycin resistance gene of pTLZ-NgHtrA#2. Using the NGSP probe, fragments having appropriate sizes are detected in the EcoRI digests on DNA from all wild-type strains tested, whereas DNA fragments roughly 1.2 kbp longer are detected in digests on DNA from the knockout mutants. The presence of this unique, new restriction fragment demonstrates the successful targeting of the NGSP locus.

Probing of the membrane with the kanamycin gene does not generate any signal in Neisseria gonorrhoeae wild-type DNA. In DNA from the knockout mutants, the kanamycin probe detects fragments having appropriate sizes in EcoRI digests. The presence of these sequences in the deletion mutants and their absence in the wild-type DNA demonstrates that the NGSP locus is successfully altered.

11. EXAMPLE

Generation and Reactivity of Monoclonal Anti-NGSP Antibodies

BALB/c mice are immunized with total outer membranes from Neisseria or with NGSP. Hybridomas for monoclonal antibodies are prepared by fusing the spleen cells from these mice to SP2/0 cells and selecting for successful hybrids with HAT containing media. Reactive hybridomas are screened using an ELISA containing detergent extracts of the total outer member of Neisseria. From this screen, hybridomas with varying levels of activity in the ELISA are selected for clonal selection, the monoclonal antibodies are assayed for reactivity to purified NGSP and total outer membranes from Neisseria by ELISA. Monoclonal antibodies are selected that react specifically to NGSP in the ELISA.

Western blots are performed as described in Example 6.4., using monoclonal antibodies.

12. Deposit of Microorganism

E. coli JM 109 containing plasmid pTLZ-NgHtrA#2 was deposited on Aug. 5, 1999 with the American Type Culture Collection (ATCC), 10801 University Boulevard, Manassas Va., 20110–2209, USA, under the provisions of the Budapest Treaty on the International Recognition of the Deposit of Microorganisms for the Purposes of Patent Procedures, and assigned number PTA-470.

The present invention is not to be limited in scope by the microorganism deposited or the specific embodiments described herein. It will be understood that variations which are functionally equivalent are within the scope of this invention. Indeed, various modifications of the invention, in addition to those shown and described herein, will become apparent to those skilled in the art from the foregoing description and accompanying drawings. Such modifications are intended to fall within the scope of the appended claims.

Various publications are cited herein, the disclosures of which are incorporated by reference in their entireties.

What is claimed is:

1. An isolated nucleic acid comprising the nucleotide sequence of SEQ ID NO. 3.

2. A pharmaceutical composition comprising the isolated nucleic acid of claim 1.

3. A recombinant expression vector comprising the isolated nucleic acid of claim 1.

4. A host cell transformed with the recombinant vector of claim 3.

5. An isolated nucleic acid comprising a nucleotide sequence encoding a polypeptide which comprises the amino acid sequence of SEQ ID NO.: 4.

* * * * *